United States Patent
Singh et al.

(10) Patent No.: US 8,883,725 B2
(45) Date of Patent: Nov. 11, 2014

(54) COMPOSITIONS AND METHODS FOR MODULATING SKIN PIGMENTATION

(75) Inventors: Suman Kumar Singh, Bradford (GB); Desmond John Tobin, Bingley (GB)

(73) Assignee: University of Bradford, Bradford (GB)

(*) Notice: Subject to any disclaimer, the term of this patent is extended or adjusted under 35 U.S.C. 154(b) by 559 days.

(21) Appl. No.: 13/063,016

(22) PCT Filed: Sep. 8, 2009

(86) PCT No.: PCT/GB2009/051139
§ 371 (c)(1),
(2), (4) Date: Apr. 20, 2011

(87) PCT Pub. No.: WO2010/029343
PCT Pub. Date: Mar. 18, 2010

(65) Prior Publication Data
US 2011/0206625 A1    Aug. 25, 2011

(30) Foreign Application Priority Data

Sep. 10, 2008 (GB) ................................... 0816507.8
May 18, 2009 (GB) ................................... 0908498.9

(51) Int. Cl.
*A61K 38/16* (2006.01)
*A61K 38/17* (2006.01)
*A61K 38/18* (2006.01)

(52) U.S. Cl.
USPC ........................... 514/8.8; 514/18.6; 514/18.8

(58) Field of Classification Search
None
See application file for complete search history.

(56) References Cited

U.S. PATENT DOCUMENTS

| | | | |
|---|---|---|---|
| 4,381,292 A | 4/1983 | Bieber et al. | |
| 4,451,570 A | 5/1984 | Royston et al. | |
| 4,618,577 A | 10/1986 | Handley et al. | |
| 4,946,778 A | 8/1990 | Ladner et al. | |
| 5,530,101 A | 6/1996 | Queen et al. | |
| 5,585,089 A | 12/1996 | Queen et al. | |
| 5,693,762 A | 12/1997 | Queen et al. | |
| 6,165,790 A | 12/2000 | Borchers et al. | |
| 6,180,370 B1 | 1/2001 | Queen et al. | |
| 8,507,501 B2* | 8/2013 | Yu et al. | 514/259.3 |
| 2006/0099186 A1* | 5/2006 | Clancy et al. | 424/93.2 |
| 2006/0239951 A1* | 10/2006 | Valentin et al. | 424/70.14 |

FOREIGN PATENT DOCUMENTS

| | | |
|---|---|---|
| WO | WO-9932619 A1 | 7/1999 |
| WO | WO-0129058 A1 | 4/2001 |
| WO | WO-03/086313 A2 | 10/2003 |
| WO | WO-2008/082525 A1 | 7/2008 |
| WO | WO-2008/143928 A1 | 11/2008 |

OTHER PUBLICATIONS

Wells, 1990, Biochemistry 29:8509-8517.*
Ngo et al., 1994, The Protein Folding Problem and tertiary Structure Prediction, Merz et al., eds., Birkhauser, Boston, pp. 491-495.*
Hair, http://www.webmd.com/skin-problems-and-treatments/picture-of-the-hair, accessed Oct. 17, 2013.*
Bateman, Alex et al., "The Pfam Protein Families Database", Nucleic Acids Research, vol. 28, No. 1, Oct. 1, 1999, 263-266.
Bertolotto, Corine et al., "Microphthalmia Gene Product as a Signal Transducer in cAMP-Induced Differentiation of Melanocytes", The Journal of Cell Biology, vol. 142, No. 3, Aug. 10, 1998, 827-835.
Botchkarev, Vladimir A., "Bone Morphogenetic Proteins and Their Antagonists in Skin and Hair Follicle Biology", Dermatology Foundation, 2002, 36-47.
Carlos, T.M. et al., "Leukocyte-endothelial adhesion molecules", Blood, 1994, 84: 2068-2101.
Elbashir, Sayda M. et al., "Duplexes of 21-nucleotide RNAs mediate RNA interference in cultured mammalian cells", Nature, May 24, 2001, vol. 411: 494-498.
Elbashir, Sayda M. et al., "RNA interference is mediated by 21-and 22-nucleotide RNAs", Genes & Development, Oct. 25, 2001, 15:188-200.
Fire, Andrew, "RNA-triggered gene silencing", TIG, Sep. 1999, vol. 15, No. 9, 358-363.
Fire, Andrew et al., "Potent and specific genetic interference by double-stranded RNA in *Caenorhabditis elegans*", Nature, Feb. 1998, vol. 391/91, 806-811.
Galibert, Marie-Dominique et al., "The Usf-1 transcription factor is a novel target for the stress-responsive p38 kinase and mediates UC-induced Tyrosinase expression", The EMBO Journal, 2001, vol. 20 No. 17, 5022-5031.
Gribskov, Michael et al., "Sigma factors from *E. coli, B. subtilis*, phage SP01, and phage T4 homologous proteins", Nucleic Acids Research, IRL Press Limited, Jul. 23, 1986, vol. 14 No. 16, 6745-6763.
Hammond, Scott M. et al., "An RNA-directed nuclease mediates post-transcriptional gene silencing in *Drosophila* cells", Nature, vol. 404, Mar. 16, 2000, 293-296.
Hogan, Brigid LM, "Bone morphogenetic proteins in development", Current Opinion in Genetics & Development, 1996, 6:432-438.
Hopp, Thomas et al. "Prediction of protein antigenic determinants from amino acid sequences", Immunology, Jun. 1981, vol. 78, No. 6, 3824-3828.

(Continued)

*Primary Examiner* — Elizabeth C Kemmerer
(74) *Attorney, Agent, or Firm* — Winstead PC

(57) ABSTRACT

The present invention relates to compositions and methods useful in studying or modulating melanin pigmentation in the skin. Particularly, the invention relates to compositions comprising a substance capable of modulating the activity or expression of ALK6 (SEQ ID 2) or Cdc42 which in turn are capable of modulation of the transfer of melanin from melanocytes to keratinocytes and potentially from keratinocytes to keratinocytes. The invention also relates to assays for identifying such compositions, and methods of modulating skin pigmentation.

11 Claims, 10 Drawing Sheets

(56) References Cited

OTHER PUBLICATIONS

Figure 1:
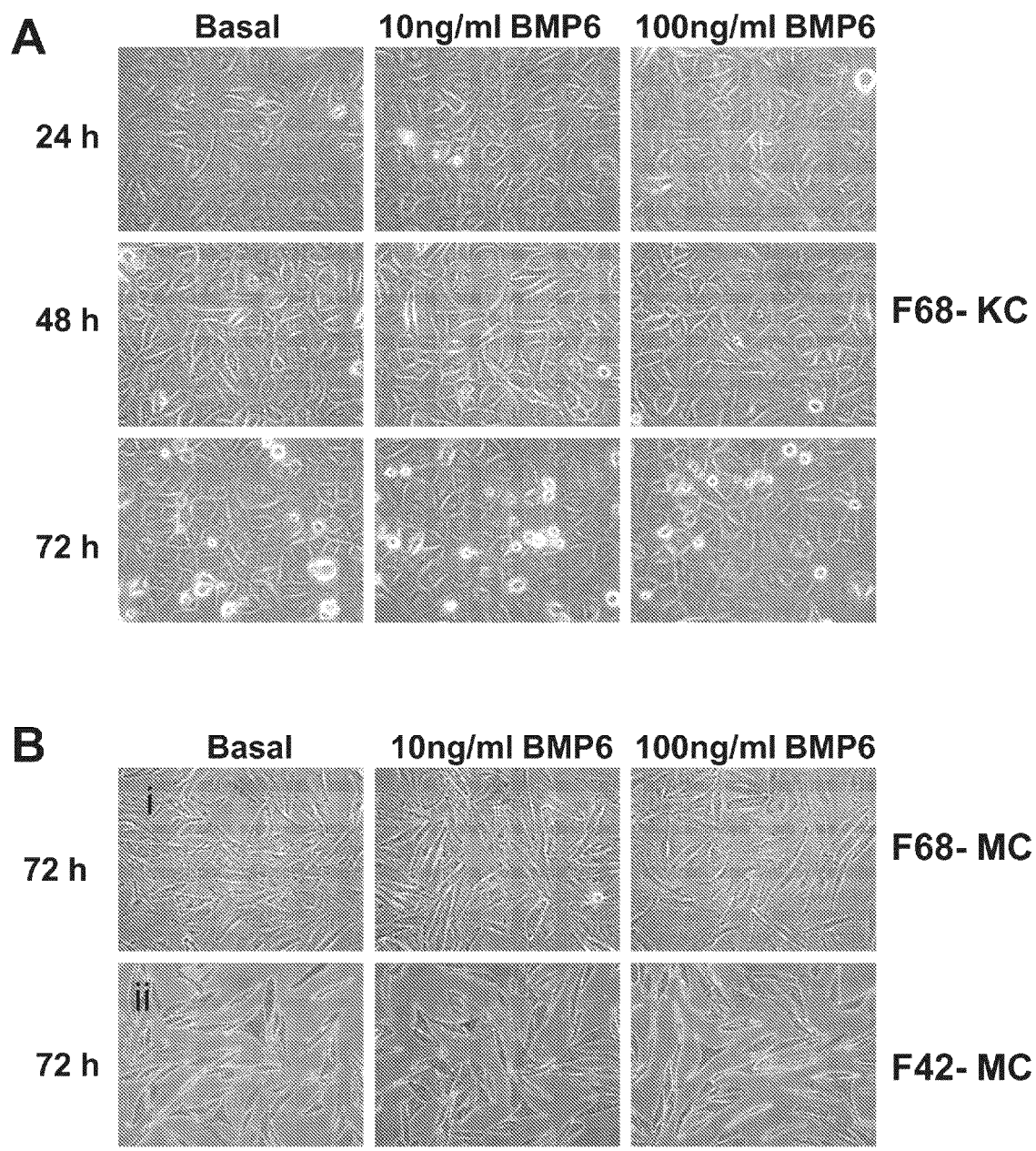

Huston, James S. et al., "Protein engineering of antibody binding sites: Recovery of specific activity in an anti-digoxin single-chain Fv analogue produced in *Escherichia coli*", Biochemistry, Aug. 1988, vol. 85, 5879-5883.

Kauser, Söbia, "Regulation of Human Epidermal Melanocyte Biology by β-Endorphin", The Journal of Investigative Dermatology, Jun. 2003, vol. 120, No. 6, 1073-1080.

Kawabata, M. et al., "Signal Transduction by Bone Morphogenetic Proteins", Cytokine & Growth Factor Reviews, 1998, vol. 9, No. 1, 49-61.

Morrison, Sherie L. et al., "Chimeric human antibody molecules: Mouse antigen-binding domains with human constant region domains", Proc. Natl. Acad. Sci, USA, Nov. 1984, vol. 81, Immunology, 6851-6855.

Morrison, Sherie, "In Vitro Antibodies: Strategies for Production and Application", Annu. Rev. Immunol. 1992, 10:239-265.

Nicholas, Hugh B. Jr. et al., "A Tutorial on Searching Sequence Databases and Sequence Scoring Methods", Biomedical Supercomputing Initiative of the Pittsburgh Supercomputing Center, Jan. 1997, 29 pages.

Panchision, David M. et al., "Sequential actions of BMP receptors control neural precursor cell production and fate", Genes & Development, 2001, 15:2094-2110.

Pi, Xinchun et al., "Sequential roles for myosin-X in BMP6-dependent filopodial extension, migration, and activation of BMP receptors", The Journal of Cell Biology, Dec. 31, 2007, vol. 179 No. 7, 1569-1582.

Scott, Glynis et al., "Filopodia are conduits for melanosome transfer to keratinocytes", Journal of Cell Science, Jan. 4, 2002, 115, 1441-1451.

Sharp, Phillip A., "RNA interference—2001", Genes & Development, 2001, 15:485-490.

Singh, Suman Kumar et al., "Human placental lipid induces melanogenesis through p38 MAPK in B16F10 mouse melanoma", Pigment Cell Res, Dec. 28, 2004, 18; 113-121.

Singh, Suman K. et al., "The silver locus product (Silv/gp100/Pmel17) as a new tool for the analysis of melanosome transfer in human melanocyte-keratinocyte co-culture", Journal compilation © Blackwell Munksgaard, Experimental Dermatology, Jan. 14, 2008, 17: 418-426.

Smalley, Keiran et al., "The involvement of p38 mitogen-activated protein kinase in the α-melanocyte stimulating hormone (α-MSH)-induced melanogenic and anti-proliferative effects in B16 murine melanoma cells", FEBS Letters 476, 2000, 198-202.

Tuschl, Thomas, "RNA Interference and Small Interfering RNAs", CHEMBIOCHEM, 2001, 2, 239-245.

Yaar, Mina et al., "Bone Morphogenetic Protein-4, a Novel Modulator of Melanogenesis", Journal of Biological Chemistry, Sep. 1, 2006, vol. 281, No. 35, 25307-25314.

Zamore, Phillip D et al., "RNAi: Double-Stranded RNA Directs the ATP-Dependent Cleavage of mRNA at 21 to 23 Nucleotide Intervals", Cell, Mar. 31, 2000, vol. 101, 25-33.

Singh, Suman K., et al, "The silver locus product (Silv/gp100/Pmel17) as a new tool for the analysis of melanosome transfer in human melanocyte-keratinocyte co-culture", Experimental Dermatology, Blackwell, Munskgaard, Copenhagen; DK, vol. 17, Mar. 6, 2008, pp. 418-426.

Pi, Xinchun, et al., "Sequential roles for myosin-X in BMP6-dependent filopodial extension, migration, and activation of BMP receptors", The Journal of Cell Biology, Rockefeller University Press, US, vol. 179, No. 7, Dec. 31, 2007, pp. 1569-1582.

Scott, Glynis, et al., "Filopodia are conduits for melanosome transfer to keratinocytes", Journal of Cell Science, Cambridge University Press, London, GB, vol. 115, No. 7, Jan. 1, 2002, pp. 1441-1451.

Ito, Yuko, et al., "Centaureidin promotes dendrite retraction of melanocytes by activating Rho", Biochimica Et Biophysica Acta—General Subjects, Elsevier Science Publishers, NL, vol. 1760, No. 3, Mar. 1, 2006, pp. 487-494.

Yaar, Mina, et al., "Bone Morphogenetic Protein-4, a Novel Modulator of Melanogenesis", Journal of Biological Chemistry, American Society for Biochemistry and Molecular Biology, Inc., US, vol. 281, No. 35, Sep. 1, 2006, pp. 25307-25314.

Lenzen, Achim, "International Search Report", for PCT/GB2009/051139, as mailed Apr. 9, 2010, 7 pages.

\* cited by examiner

Supplement-1

SEQUENCE LISTING

```
<160> NUMBER OF SEQ ID NOS: 10

<210> SEQ ID NO 1
<211> LENGTH: 513
<212> TYPE: PRT
<213> ORGANISM: Homo sapiens

<400> SEQUENCE: 1

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
                20                  25                  30

Ala Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
        50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285
```

```
Asp Leu Phe Leu Leu Asp Thr Arg Val Val Trp Ala Ser Glu Glu Gly
            290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
            355                 360                 365

His Val Arg Thr Thr Arg Ser Ala Ser Ser Arg Arg Gln Gln Ser
            370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
            435                 440                 445

Leu Asn Ala His Met Asn Ala Thr Asn His Ala Ile Val Gln Thr Leu
            450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His

<210> SEQ ID NO 2
<211> LENGTH: 502
<212> TYPE: PRT
<213> ORGANISM: Homo sapiens

<400> SEQUENCE: 2

Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
            35                  40                  45

Thr Asp Gly Tyr Cys Phe Thr Met Ile Glu Glu Asp Asp Ser Gly Leu
        50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140
```

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
            165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
            195                 200                 205

Gln Ile Gly Lys Gly Arg Tyr Gly Glu Val Trp Met Gly Lys Trp Arg
210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
            245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
            275                 280                 285

Asp Tyr Leu Lys Ser Thr Thr Leu Asp Ala Lys Ser Met Leu Lys Leu
290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
            325                 330                 335

Asn Ile Leu Val Lys Lys Asn Gly Thr Cys Cys Ile Ala Asp Leu Gly
            340                 345                 350

Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
            405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
            485                 490                 495

Ser Gln Asp Ile Lys Leu
            500

<210> SEQ ID NO 3
<211> LENGTH: 213
<212> TYPE: PRT
<213> ORGANISM: Homo sapiens

<400> SEQUENCE: 3

```
Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
            20                  25                  30

Ala Thr Glu Ile Ile Pro Glu Leu Gly Glu Tyr Pro Glu Pro Pro Pro
        35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65              70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
            195                 200                 205

Leu Glu Asn Ala Tyr
    210

<210> SEQ ID NO 4
<211> LENGTH: 532
<212> TYPE: PRT
<213> ORGANISM: Homo sapiens

<400> SEQUENCE: 4

Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Lys Ser Glu Asn Gly Val
        35                  40                  45

Thr Leu Ala Pro Glu Asp Thr Leu Pro Phe Leu Lys Cys Tyr Cys Ser
    50                  55                  60

Gly His Cys Pro Asp Asp Ala Ile Asn Asn Thr Cys Ile Thr Asn Gly
65              70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
    130                 135                 140

Pro Phe Phe Asp Gly Ser Ile Arg Trp Leu Val Leu Leu Ile Ser Met
145                 150                 155                 160
```

Ala Val Cys Ile Ile Ala Met Ile Ile Phe Ser Ser Cys Phe Cys Tyr
             165                 170                 175

Lys His Tyr Cys Lys Ser Ile Ser Ser Arg Arg Tyr Asn Arg Asp
             180                 185                 190

Leu Glu Gln Asp Glu Ala Phe Ile Pro Val Gly Glu Ser Leu Lys Asp
             195                 200                 205

Leu Ile Asp Gln Ser Gln Ser Ser Gly Ser Gly Ser Gly Leu Pro Leu
             210                 215                 220

Leu Val Gln Arg Thr Ile Ala Lys Gln Ile Gln Met Val Arg Gln Val
225                  230                 235                 240

Gly Lys Gly Arg Tyr Gly Glu Val Trp Met Gly Lys Trp Arg Gly Glu
                 245                 250                 255

Lys Val Ala Val Lys Val Phe Phe Thr Thr Glu Glu Ala Ser Trp Phe
                 260                 265                 270

Arg Glu Thr Glu Ile Tyr Gln Thr Val Leu Met Arg His Glu Asn Ile
                 275                 280                 285

Leu Gly Phe Ile Ala Ala Asp Ile Lys Gly Thr Gly Ser Trp Thr Gln
290                  295                 300

Leu Tyr Leu Ile Thr Asp Tyr His Glu Asn Gly Ser Leu Tyr Asp Phe
305                  310                 315                 320

Leu Lys Cys Ala Thr Leu Asp Thr Arg Ala Leu Leu Lys Leu Ala Tyr
                 325                 330                 335

Ser Ala Ala Cys Gly Leu Cys His Leu His Thr Glu Ile Tyr Gly Thr
                 340                 345                 350

Gln Gly Lys Pro Ala Ile Ala His Arg Asp Leu Lys Ser Lys Asn Ile
                 355                 360                 365

Leu Ile Lys Lys Asn Gly Ser Cys Cys Ile Ala Asp Leu Gly Leu Ala
370                  375                 380

Val Lys Phe Asn Ser Asp Thr Asn Glu Val Asp Val Pro Leu Asn Thr
385                  390                 395                 400

Arg Val Gly Thr Lys Arg Tyr Met Ala Pro Glu Val Leu Asp Glu Ser
                 405                 410                 415

Leu Asn Lys Asn His Phe Gln Pro Tyr Ile Met Ala Asp Ile Tyr Ser
                 420                 425                 430

Phe Gly Leu Ile Ile Trp Glu Met Ala Arg Arg Cys Ile Thr Gly Gly
                 435                 440                 445

Ile Val Glu Glu Tyr Gln Leu Pro Tyr Tyr Asn Met Val Pro Ser Asp
450                  455                 460

Pro Ser Tyr Glu Asp Met Arg Glu Val Val Cys Val Lys Arg Leu Arg
465                  470                 475                 480

Pro Ile Val Ser Asn Arg Trp Asn Ser Asp Glu Cys Leu Arg Ala Val
                 485                 490                 495

Leu Lys Leu Met Ser Glu Cys Trp Ala His Asn Pro Ala Ser Arg Leu
                 500                 505                 510

Thr Ala Leu Arg Ile Lys Lys Thr Leu Ala Lys Met Val Glu Ser Gln
                 515                 520                 525

Asp Val Lys Ile
             530

<210> SEQ ID NO 5
<211> LENGTH: 22
<212> TYPE: DNA
<213> ORGANISM: Artificial Sequence
<220> FEATURE:

-continued

```
<223> OTHER INFORMATION: Primer

<400> SEQUENCE: 5
gcccgtgacc tgaaggctgt ca                                              22

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
tgcttttagt atgatgccga cacca                                           25

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
caccccacaa atcctaac                                                   18

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cctactctat tgcctaagcc                                                 20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gaaggtgaag gtcggagtac a                                               21

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
ttgttttgga gggatctcg                                                  19
```

COMPOSITIONS AND METHODS FOR MODULATING SKIN PIGMENTATION

The present invention relates to compositions and methods useful in studying or modulating melanin pigmentation in the skin. Particularly, but not exclusively, the invention relates to compositions capable of modulation of the transfer of melanin from melanocytes to keratinocytes and potentially from keratinocytes to keratinocytes, assays for identifying such compositions, and methods of modulating skin pigmentation.

Melanocytes are neural crest-derived cells distributed along the basal layer of the epidermis and hair bulb. These cells synthesize melanin pigment within unique melanocyte-specific organelles called melanosomes. For skin and hair to become pigmented this melanin must be transferred from melanocytes to adjacent keratinocytes. Mammalian skin and hair/wool/fur colour is determined by melanin quantity and quality (brown/black eumelanin or red/yellow pheomelanin) in a process that involves a large number of steps regulated at multiple control points by a range of different molecules and compounds. The last couple of decades have seen much progress in our understanding of the molecular control of melanin synthesis and melanosome biogenesis/maturation. However, a significant gap in our knowledge centres on how melanin transfer is controlled—a primary clinical/cosmetic interest as this process ultimately controls the level of pigmentation perceived at the skin surface and along the hair fiber.

In this application a novel mechanism that controls melanin transfer from human cutaneous melanocytes to human cutaneous keratinocytes is described. This mechanism involves the action of BMP6, which stimulates this process in a dose-dependent fashion.

Bone morphogenetic proteins (BMPs) are secreted signalling molecules that belong to the TGF-β superfamily. They play important roles in cell proliferation, differentiation, motility, adhesion and cell death (Hogan 1996). More than 20 distinct BMP family members have been described to date, and each exerts it biological activity via interaction with specific BMP receptors (Wozney et al., 1988). BMP signalling operates at multiple levels depending on BMP type, presence of antagonist(s), development stage of target tissue, and target cell receptor type (Botchkarev 2003). BMPs bind two transmembrane receptor families, multiple BMP receptor (BMPR)I and a single BMPRII (Hogan 1996). Interestingly, to initiate signalling, BMP has to bind both receptors, inducing phosphorylation of an intracellular domain in BMPRI by BMP-RII and activating intracellular signal transduction.

BMPs are powerful regulators of cutaneous development, and they also play important roles in the control of epidermal homeostasis, hair follicle growth, and melanogenesis in normal postnatal skin (Botchkarev 2003). Melanocytes are neural crest-derived cells that migrate to the epidermis and hair follicles during embryogenesis and subsequently synthesize and distribute melanin to surrounding keratinocytes (Halaban et al 2003). Interestingly, there are several BMPRI receptors, BMPRIA (ALK3; Seq ID 4), BMPRIB (ALK6; Seq ID 2), and ActR-I (ALK2) (Kawabata et al., 1998) and in neural precursor cells signalling through ALK3 induces their proliferation while ALK6 induces their differentiation (Panchision et al., 2001), suggesting that receptor expression determines the BMP effect on cells.

The role of BMP4 in melanocyte biology was first shown by the Gilchrest group in a study showing that this particular BMP family member acted as an autocrine inhibitor of melanogenesis in normal human melanocytes by inhibiting the expression and activity of the rate-limiting enzyme (tyrosinase) in melanocytes (Yaar et al., 2006).

However, the involvement of other BMP proteins in melanocyte biology (e.g., melanogenesis and/or melanin transfer) has not been reported so far. While much is known about the regulation of melanogenesis (i.e. melanin synthesis) in melanocytes, our knowledge of how melanosomes transfer from melanocytes to keratinocytes is still very limited. In addition to a role for cyto-phagocytosis, there is increasing evidence to support melanosome transfer via filopodia which can interact with keratinocyte plasma membrane (Scott et al., 2002, Singh et al., 2008). Importantly structures consistent with filopodia arising from the sides and tips of melanocyte dendrites and which contain melanosomes within their lumina, have already been reported in human skin in situ as well as in vitro (Scott et al., 2002).

According to a first aspect of the present invention there is provided a method of modulating melanin pigmentation of the skin and/or hair of a subject, the method comprising administering to a subject a composition comprising a substance capable of modulating the activity or expression of ALK6 (SEQ ID 2) or Cdc42.

In a preferred embodiment of the present invention the substance modulates the expression of Cdc42 through modulating the activity of ALK6.

In a preferred embodiment of the present invention the method involves application of the composition to the outer surface of the skin and/or hair of a subject.

In order to modulate pigmentation of the skin, there are two main approaches: modulating melanogenesis and modulating transfer of melanin. The present invention can involve one, other or both of these approaches. However, methods which modulate melanin transfer are of particular interest as the present inventors have discovered that melanin transfer can be effectively targeted. Given that it is a further "downstream" process than melanogenesis, it is a more attractive target in terms of avoiding adverse effects.

Suitably the method is a cosmetic method, which is useful for cosmetic lightening or darkening of skin and/or hair colour through modulating the level of melanin pigmentation of the skin and/or hair.

Alternatively the method may be used to provide a degree of photoprotection to the subject. It is well known that melanin protects the skin from many of the damaging effects of ultraviolet radiation. Accordingly, increasing the amount of melanin in the skin of a subject may be significant in reducing sunlight induced damage, e.g. mutation of a cell potentially leading to cancer or premature ageing.

In another alternative, the method may be used to treat a medical condition associated with abnormal pigmentation of the skin. Such treatment may be curative, or it might be used in order to lesson symptoms. Diseases or medical conditions associated with altered pigmentation of the skin which could be treated include hyperpigmentation (e.g., melasma, chloasma, senile lentigo, solar lentigo, ephelides, post-inflammatory hyperpigmentation) and hypopigmentation (e.g., vitiligo, and post-inflammatory hypopigmentation) and pigmentation loss as a result of skin damage.

In one embodiment the substance is capable of increasing the activity or expression of ALK6 relative to normal physiological levels, i.e. an ALK6 agonist. In particular embodiments the substance is capable of increasing the activity or expression of ALK6 in a manner which increases melanin transfer. An increase in ALK6 activity would lead to increased melanin in the skin and/or hair.

In another embodiment the substance is capable of decreasing the activity or expression of ALK6 relative to normal physiological levels, i.e. an ALK6 antagonist. In particular embodiments the substance is capable of decreasing the activity or expression of ALK6 in a manner which decreases melanin transfer. A decrease in ALK6 activity would lead to decreased melanin in the skin and/or hair.

In one embodiment, the present invention method involves application of a composition comprising a BMP6 polypeptide (accession number NM_001718; Seq ID 1) or a fragment or variant thereof, wherein said fragment or variant is functionally active.

A fragment or variant can be said to be functionally active where it is able to activate ALK6 at least 50% as efficiently as wild type BMP6, though lower levels of activity may still be useful. More preferably such a fragment or variant should be at least 75% as active as wild type BMP6, especially 90% as active as wild type BMP6. In particular, "active" in this context can mean the ability to stimulate the transfer of melanin from melanocytes to keratinocytes in the assays described below.

A "functionally active" BMP6 fragment or variant exhibits the ability to increase melanogenesis or melanin transfer as determined using the assays described later. The functional activity of BMP6 proteins, variants and fragments can be assayed by various methods known to one skilled in the art (Current Protocols in Protein Science (1998) Coligan et al., eds., John Wiley & Sons, Inc., Somerset, N.J.) and as further discussed below.

For purposes herein, functionally active fragments can include those fragments that comprise one or more structural domains of a BMP6, such as a binding domain, providing said domain is capable of the desired activity. Protein domains can be identified using the PFAM program (Bateman A., et al., Nucleic Acids Res, 1999, 27: 260-2). In some embodiments, preferred fragments are functionally active, domain-containing fragments comprising at least 25 contiguous amino acids, preferably at least 50, more preferably 75, and most preferably at least 100 contiguous amino acids of a BMP6 active domain. In further preferred embodiments, the fragment comprises the entire functionally active domain.

The functionally active fragment or variant includes recombinant BMP6 polypeptides and functionally active fragments or variants thereof, including those encoded by a BMP6-encoding nucleic acid.

The functionally active BMP6 polypeptide could theoretically encompass the BMP6 precursor protein (accession number P22004) (SEQ ID 1). The mature BMP6 polypeptide is believed to include amino acids 374-513 of the same.

Functionally active fragments can include polypeptides comprising amino acids 382-513, 388-513 and 412-513 of the BMP6 precursor (SEQ ID 1). The term "BMP6-encoding nucleic acid" refers to a DNA or RNA molecule that encodes a BMP6 polypeptide.

Preferably, the BMP6 polypeptide or nucleic acid or variant or fragment thereof is from a human, but can also be a homolog or derivative thereof.

Preferably said variant or fragment thereof has at least 70% sequence identity, preferably at least 80%, more preferably 85%, still more preferably 90%, and most preferably at least 95% sequence identity with human BMP6 or the sequence encoding BMP6 (NM_001718).

As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2. 0al9 (Altschul et al., J. Mol. Biol. (1997) 215: 403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2: 482-489; database: European Bioinformatics Institute; Smith and Waterman, 1981, J. of Molec. Biol., 147: 195-197; Nicholas et al., 1998, "A Tutorial on Searching Sequence Databases and Sequence Scoring Methods" (www.psc.edu) and references cited therein; W. R. Pearson, 1991, Genomics 11: 635-650). This algorithm can be applied to amino acid sequences by using the scoring matrix developed by Dayhoff (Dayhoff: Atlas of Protein Sequences and Structure, M. O. Dayhoff ed., 5 suppl. 3: 353-358, National Biomedical Research Foundation, Washington, D.C., USA), and normalized by Gribskov (Gribskov 1986 Nucl. Acids Res. 14 (6): 6745-6763). The Smith-Waterman algorithm may be employed where default parameters are used for scoring (for example, gap open penalty of 12, gap extension penalty of two). From the data generated, the "Match" value reflects "sequence identity".

Derivative nucleic acid molecules of the subject nucleic acid molecules include sequences that hybridize to the nucleic acid sequence encoding BMP6. The stringency of hybridization can be controlled by temperature, ionic strength, pH, and the presence of denaturing agents such as formamide during hybridization and washing. Conditions routinely used are set out in readily available procedure texts (e.g. Current Protocol in Molecular Biology, Vol. 1, Chap. 2.10, John Wiley & Sons, Publishers (1994); Sambrook et al., Molecular Cloning, Cold Spring Harbor (1989)).

In some embodiments, a nucleic acid molecule of the invention is capable of hybridizing to a nucleic acid molecule containing the nucleotide sequence of a BMP6 under high stringency hybridization conditions that are: prehybridization of filters containing nucleic acid for 8 hours to overnight at 65 C in a solution comprising 6× single strength citrate (SSC) (1×SSC is 0.15 M NaCl, 0.015 M Na citrate; pH 7.0), 5×Denhardt's solution, 0.05% sodium pyrophosphate and 100 g/ml herring sperm DNA; hybridization for 18-20 hours at 65 C in a solution containing 6×SSC, 1×Denhardt's solution, 100 μg/ml yeast tRNA and 0.05% sodium pyrophosphate; and washing of filters at 65 C for 1 hr in a solution containing 0.1×SSC and 0.1% SDS (sodium dodecyl sulfate).

In other embodiments, moderately stringent hybridization conditions are used that are: pretreatment of filters containing nucleic acid for 6 h at 40 C in a solution containing 35% formamide, 5×SSC, 50 mM Tris-HCl (pH7.5), 5 mM EDTA, 0.1% PVP, 0.1% Ficoll, 1% BSA, and 500 µg/ml denatured salmon sperm DNA; hybridization for 18-20 h at 40 C in a solution containing 35% formamide, 5×SSC, 50 mM Tris-HCl (pH7.5), 5 mM EDTA, 0.02% PVP, 0.02% Ficoll, 0.2% BSA, 100, µg/ml salmon sperm DNA, and 10% (wt/vol) dextran sulfate; followed by washing twice for 1 hour at 55 C in a solution containing 2×SSC and 0.1% SDS.

Alternatively, low stringency conditions can be used that are: incubation for 8 hours to overnight at 37 C in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37 C for 1 hour.

In another embodiment the method involves the application of a composition comprising a compound capable of binding to BMP6 and inactivating it. Accordingly, the present invention can relate to antagonists of BMP6. For example, the compound might be an antibody or a fragment thereof which is capable of binding to BMP6.

Antibodies that specifically bind BMP6 polypeptides can be generated using known methods. Preferably the antibody is specific to a mammalian ortholog of BMP6 polypeptide, and more preferably, to human BMP6. Antibodies may be polyclonal, monoclonal (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Epitopes of BMP6 which are particularly antigenic can be selected, for example, by routine screening of BMP6 polypeptides for antigenicity or by applying a theoretical method for selecting antigenic regions of a protein (Hopp and Wood (1981), Proc. Natl. Acad. Sci. U.S.A. 78: 3824-28; Hopp and Wood, (1983) Mol. Immunol. 20: 483-89; Sutcliffe et al., (1983) Science 219: 660-66) to the amino acid sequence of a BMP6. Monoclonal antibodies with affinities of $10^8 M^{-1}$ preferably $10^9 M^{-1}$ to $10^{10} M^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577).

Antibodies may be generated against crude cell extracts of BMP6 or substantially purified fragments thereof. If BMP6 fragments are used, they preferably comprise at least 10, and more preferably, at least 20 contiguous amino acids of a BMP6 protein. BMP6-specific antigens and/or immunogens can be coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of BMP6-specific antibodies is assayed by an appropriate assay such as a solid phase enzyme-linked immunosorbant assay (ELISA) using immobilized corresponding BMP6 polypeptides. Other assays, such as radioimmunoassays or fluorescent assays might also be used.

Chimeric antibodies specific to BMP6 polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81: 6851-6855; Neuberger et al., Nature (1984) 312: 604-608; Takeda et al., Nature (1985) 31: 452-454).

Humanized antibodies, which are a form of chimeric antibodies, can be generated by grafting complementary-determining regions (CDRs) (Carlos, T. M., J. M. Harlan. 1994. Blood 84: 2068-2101) of mouse antibodies into a background of human framework regions and constant regions by recombinant DNA technology (Riechmann L M, et al., 1988 Nature 323: 323-327). Humanized antibodies contain murine sequences and human sequences, and thus further reduce or eliminate immunogenicity, while retaining the antibody specificities (Co M S, and Queen C. 1991 Nature 351: 501-501; Morrison SL. 1992 Ann. Rev. Immun. 10: 239-265). Humanized antibodies and methods of their production are well-known in the art (U.S. Pat. Nos. 5,530,101, 5,585,089, 5,693,762, and 6,180,370).

BMP6-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242: 423-426; Huston et al., Proc. Natl. Acad. Sci. USA (1988) 85: 5879-5883; and Ward et al., Nature (1989) 334: 544-546).

Other suitable techniques for antibody production involve in vitro exposure of lymphocytes to the antigenic polypeptides or alternatively to selection of libraries of antibodies in phage or similar vectors (Huse et al., Science (1989) 246: 1275-1281).

The polypeptides and antibodies of the present invention may be used with or without modification. Frequently, antibodies will be labelled by joining, either covalently or non-covalently, a substance that provides for a detectable signal, or that is toxic to cells that express the targeted protein (Menard S, et al., Int J. Biol Markers (1989) 4: 131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816, 567). Antibodies to cytoplasmic polypeptides may be delivered and reach their targets by conjugation with membrane-penetrating toxin proteins (U.S. Pat. No. 6,086,900).

In another embodiment the method involves the application of a composition comprising a compound capable of binding to ALK6 and either activating or blocking its activity. For example, such a compound may be a an antibody or a fragment thereof which is capable of binding to ALK6. As such, the present invention can comprise agonists or antagonists of ALK6. For example, an antibody might bind ALK6 and prevent the binding of BMP6, thus preventing BMP6 from activating ALK6 and driving melanogenesis or melanin transfer. Details of well known techniques of antibody generation are set out above.

In another embodiment the method involves the application of a composition comprising a nucleic acid capable of modulating the expression of ALK6 or Cdc42 through interaction with DNA or RNA coding for ALK6 or Cdc42 or a functional portion thereof. In a preferred embodiment the nucleic acid is an RNA molecule, especially an RNA molecule capable of targeted antisense interaction or RNA interference against mRNA encoding ALK6 or Cdc42_. For example, a suitable RNAi molecule for targeting Cdc42 mRNA can be 5'-GAUAACUCACCACUGUCCATT-3' and 5'-UGGACAGUGGUGAGUUAUCTT-3' oligoribonucleotides; or 5'-GACUCCUUUCUUGCUUGUUTT-3' and 5'-AACAAGCAAGAAAGGAGUCTT-3' oligoribonucleotides can be used to inhibit Cdc42, or other such appropriate and specific sequence. It is within the skills of the person skilled in the art to determine other suitable sequences which would exhibit RNAi against ALK6 or Cdc42 mRNA.

RNAi is the process of sequence-specific, post-transcriptional gene silencing in animals and plants, initiated by double-stranded RNA (dsRNA) that is homologous in sequence to the silenced gene. Methods relating to the use of RNAi to silence genes in C. elegans, Drosophila, plants, and humans are known in the art (Fire A, et al., 1998 Nature 391: 806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411: 494-498; Novina CD and Sharp P. 2004 Nature 430: 161-164; Soutschek J et al 2004 Nature 432: 173-178).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med. Chem. (1993) 36: 1923-1937; Tonkinson J L et al., Antisense Oligodeoxynucleotides as Clinical Therapeutic Agents, Cancer Invest. (1996) 14: 54-65).

In one embodiment the method involves the application of a composition identified by the methods of identifying substances that affect ALK6 or Cdc42 set out below.

In a preferred embodiment of the present invention the substance is an antagonist of ALK6. Some ALK6 antagonists which may be suitable for use in the present invention include sclerostin, chordin-like and follistatin-related protein (FSRP). In a particularly preferred embodiment the antagonist is sclerostin (SEQ ID 3).

Small molecules are often preferred to modulate function of proteins with enzymatic function, and/or containing protein interaction domains. Chemical agents, referred to in the art as "small molecule" compounds are typically organic, non-peptide molecules, having a molecular weight up to 10,000, preferably up to 5,000, more preferably up to 1,000, and most preferably up to 500 daltons. This class of modulators includes chemically synthesized molecules, for instance, compounds from combinatorial chemical libraries. Synthetic compounds may be rationally designed or identified based on known or inferred properties of the ALK6 protein or may be identified by screening compound libraries. Alternative appropriate modulators of this class are natural products, particularly secondary metabolites from organisms such as plants or fungi, which can also be identified by screening compound libraries for ALK6-modulating activity. Methods for generating and obtaining compounds are well known in the art (Schreiber S L, Science (2000) 151: 1964-1969; Radmann J and Gunther J, Science (2000) 151: 1947-1948).

Small molecule modulators identified from screening assays, as described below, can be used as lead compounds from which candidate clinical compounds may be designed, optimized, and synthesized. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Antagonists of ALK6 may be able to inhibit the transfer of melanin from melanocytes to keratinocytes, thereby reducing skin and/or hair pigmentation. On the other hand agonists of ALK6 may be capable of enhancing the transfer of melanin from melanocytes to keratinocytes, thereby increasing skin and hair pigmentation. Both of these effects can be desirable from a cosmetic point of view, and additionally there may be medical benefits from such an effect. For example it is currently desirable in western Europe and the United States (and elsewhere) to have a sun tanned appearance for cosmetic reasons. In some countries of Asia it is desirable to have a relatively pale appearance for cosmetic reasons. Additionally, given that melanin is involved in protecting the skin from the damaging effects of the sun, it may be desirable to increase melanin content of the skin from a protective point of view.

It is preferred that the subject is a mammal, preferably a primate and especially a human.

In another aspect the present invention provides a composition comprising a substance capable of modulating the activity or expression of ALK6 or Cdc42 for use in modulation of the pigmentation of the skin and/or hair of a subject. Details of suitable substances are provided above, and the modulation may be for cosmetic or for therapeutic purposes.

Particularly preferred substances include BMP6 or functionally active variants or fragments thereof, and sclerostin.

In another aspect the present invention provides use of a composition comprising a substance capable of modulating the activity or expression of ALK6 or Cdc42 in the manufacture of a medicament for the treatment of a disease associated with abnormal pigmentation of the skin. Such treatment may be curative, or it might be in order to lessen symptoms.

It is generally desirable that compositions according to the present inventions are suitable for topical application to the skin. Any common topical formulation such as a solution, suspension, gel, cream, ointment or salve and the like may be employed. Preparation of such topical formulations are described in the art of pharmaceutical formulations as exemplified, for example, by Gennaro et al. (1995) Remington's Pharmaceutical Sciences, Mack Publishing. For topical application, the compositions could also be administered as a powder or spray, particularly in aerosol form.

According to a further aspect the present invention provides a method of assessing the ability of a substance to modulate the transfer of melanin from a melanocyte to a keratinocyte or potentially from keratinocyte to keratinocyte, the method comprising the steps of:

provide a test substance; and determining the ability of the test substance to interact with ALK6.

In some embodiments, the method involves determining the ability of a substance to bind to ALK6. The ALK6 may be on a cell, or it may be provided on a support.

Preferably the method involves providing a cell expressing ALK6 and determining the ability of the test substance to interact with the ALK6 expressed by said cell, especially ALK6 expressed on the surface of the cell.

Preferably the cell expressing ALK6 is a melanocyte.

By determining the ability of a test substance to interact with ALK6 it is possible to identify substances which have the potential for being active in modulating melanin transfer or melanogenesis.

Preferably the method of the present invention involves determining the ability of the test substance to modulate the activity and/or expression of ALK6.

In one embodiment the method may involve determining the ability of the test substance to activate ALK6, i.e. determining whether the test substance is an agonist of ALK6.

In an alternative embodiment the method may involve determining the ability of the test substance to deactivate ALK6, i.e. determining whether the test substance is an antagonist of ALK6.

There are a number of ways in which the person skilled in the art could determine whether a test substance is capable of modulating the activity of ALK6. For example it is possible to determine the effect of the test substance on downstream signalling molecules which are effected by ALK6 activation. Alternatively, it would be possible to determine the effect of a test substance on the expression of mRNAs or proteins which are effected by ALK6 activation. This could involve determining, for example, a) recruitment of R-Smads (receptor regulated Smads, Smad-1, -5, -8) and its subsequent phosphorylation upon binding to ALK6; b) blocking of activation of R-Smads by inhibitory Smads (I-Smads), e.g. Smads 6 and 7; or c) selective degradation of ALK6 by Smurfs (Smad ubiquitination regulatory factors).

There are also a number of ways in which the person skilled in the art could determine the ability of a substance to increase expression of ALK6. For example, the person skilled in the art could quantitatively determine ALK6 mRNA levels in the cells (e.g. using quantitative rtPCR), or could quantitatively determine protein expression on the surface of a cell (e.g. using immunofluorescence techniques, ELISA, two-dimensional electrophoresis or mass-spectrometric methods).

In one embodiment, the method may involve the step of determining the ability of the test substance to interact with ALK6 by determining the affect of the test substance on the expression or activation of Cdc42, preferably the expression of Cdc42. Methods of determining the expression of Cdc42 include measuring the amount of Cdc42 protein in or on the cell, or determining the amount of a precursor in the synthesis of Cdc42 protein, for example mRNA which codes for Cdc42. Techniques required to determine the level of expression of Cdc42 protein or Cdc42 mRNA levels would be apparent to the person skilled in the art. Techniques to determine protein levels may involve immunostaining (e.g., immunofluorescence, western blotting), ELISA, two-dimensional electrophoresis or mass-spectrometric methods. Techniques to determine mRNA levels might involve northern blotting, reverse transcriptase PCR, quantitative PCR, microarrays or Affymetrix® chips.

In particular, the present invention is concerned with substances which are capable of interacting with ALK6 in a manner which affects melanogenesis or melanin transfer. Accordingly, determining the effect of a test substance on melanogenesis or melanin transfer is particularly desirable. Methods of achieving this are set out in detail in the present application, for example determining the effect of a substance on the number of melanosomes transferred from a melanocyte to a keratinocyte or potentially from keratinocyte to keratinocyte. This may be achieved using the immunostaining techniques described in the present application.

The method of the present invention may involve the step of providing BMP6. By providing BMP6 in the method, it is possible to determine the ability of a test substance to modulate the activity of ALK6 is the presence of its biological ligand. Such a method may be more relevant to physiological conditions as it assesses the ability of a compound to interact with ALK6 in competition with BMP6.

In a further aspect the present invention provides a method of assessing the ability of a substance to modulate the transfer of melanin from a melanocyte to a keratinocyte, or potentially from keratinocyte to keratinocyte, the method comprising the steps of:

providing a test substance;

providing a cell expressing Cdc42; and determining the ability of the test substance to modulate the activity and/or expression of Cdc42.

Preferably the cell expressing Cdc42 is a melanocyte or a keratinocyte, more preferably a melanocyte.

The method may involve comparing the activity and/or expression of Cdc42 in a cell treated with the test substance with the activity and/or expression of Cdc42 in a control cell.

The level of expression of Cdc42 may be determined by many methods apparent to the person skilled in the art. In embodiments of the present invention the expression may be determined using immunofluorescence, western blotting or by determining the level of Cdc42 mRNA. As mentioned above, other suitable methods would be apparent to the person skilled in the art.

Embodiments of the present invention will now be described, by way of example only, with reference to the accompanying drawings in which:

FIGS. 1 A and B show the results of assessment of epidermal keratinocyte and epidermal melanocyte cytotoxicity to BMP6 incubation in vitro.

A. Normal human epidermal keratinocyte culture (Female-68; p2) were treated for 24 h, 48 h and 72 h with 10 ng/ml and 100 ng/ml of BMP6.

B. Normal human epidermal melanocytes cultures (i) Female-68; p4 and (ii) Female-42; p3 were treated 72 h with 10 ng/ml and 100 ng/ml of BMP6. Cytotoxicity was assessed by cell death and cytopathologic change in morphology. No cytotoxic effects can be seen.

Figure 2:
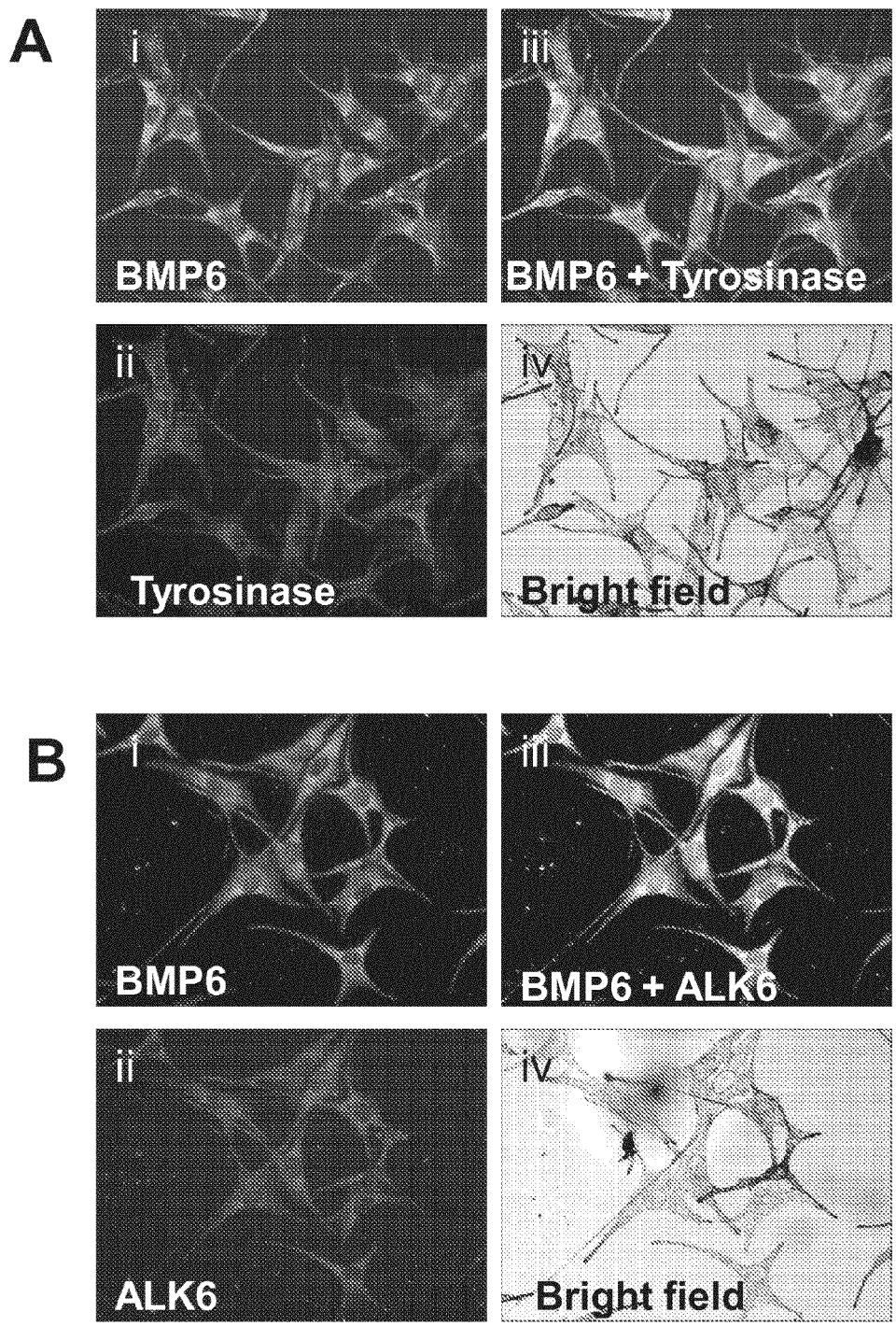

FIGS. 2 A and B show the results of detection of BMP6 and ALK6 protein expression in normal human epidermal melanocytes.

A. Double-immunolabeling for (i) BMP6 (green); (ii) tyrosinase (red) and (iii) merged image of BMP6 and tyrosinase, confirming BMP6 protein expression in human epidermal melanocytes (F39-MC). (iv) shows the corresponding bright-field image.

B. Double-immunolabeling for (i) BMP6 (green), (ii) ALK6 (red) and (iii) showing co-localization of BMP6 and ALK6 (yellow) in human epidermal melanocytes (F39-MC). (iv) shows the corresponding bright-field image.

Figure 3:
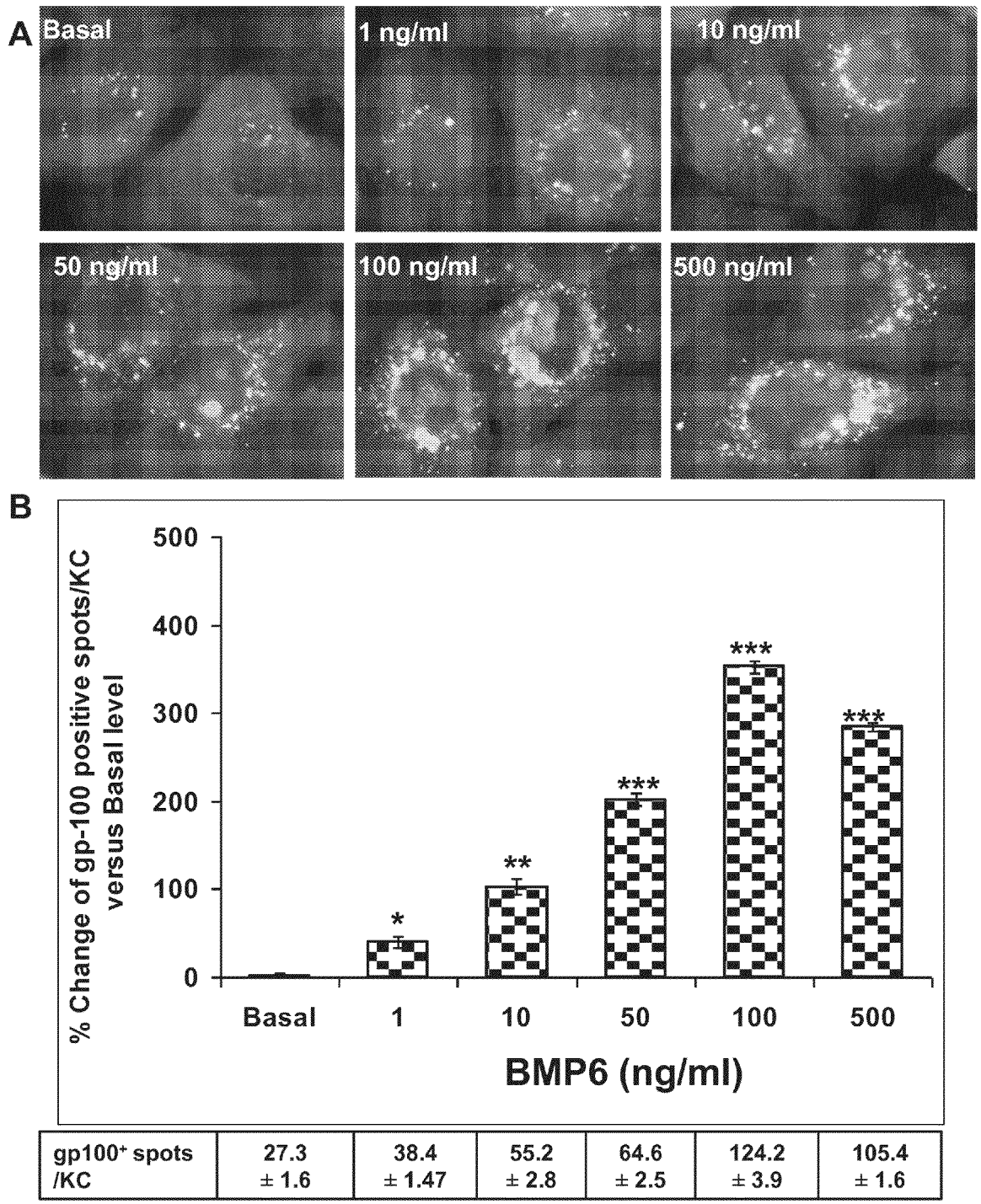

FIGS. 3 A and B show the results of quantitative analysis of dose-dependent BMP6-stimulated melanosome transfer in epidermal melanocyte-keratinocyte co-culture.
- A. Double-immunofluorescence was performed on matched melanocyte-keratinocyte co-cultures (F39 MC-KC) stimulated with increasing concentrations of BMP-6 for 24 h (1, 10, 50, 100 and 500 ng/ml). Double-immunolabelling with anti-gp100 antibody (green) and anti-cytokeratin antibody (red) showed a marked dose-dependent increase in the number of fluorescent spots transferred to keratinocyte. Nuclei were stained with DAPI.
- B. Quantification of transferred melanosomes in five randomly-selected microscopic fields (total 20 cells per field) for each of the different treatment groups. Values were expressed as percentage increase in the number of gp100-positive spots per keratinocyte compared to unstimulated control levels. Means are ±SEM of three independent experiments with *=P<0.05, =P<0.01, and *=P<0.001.

Figure 4:
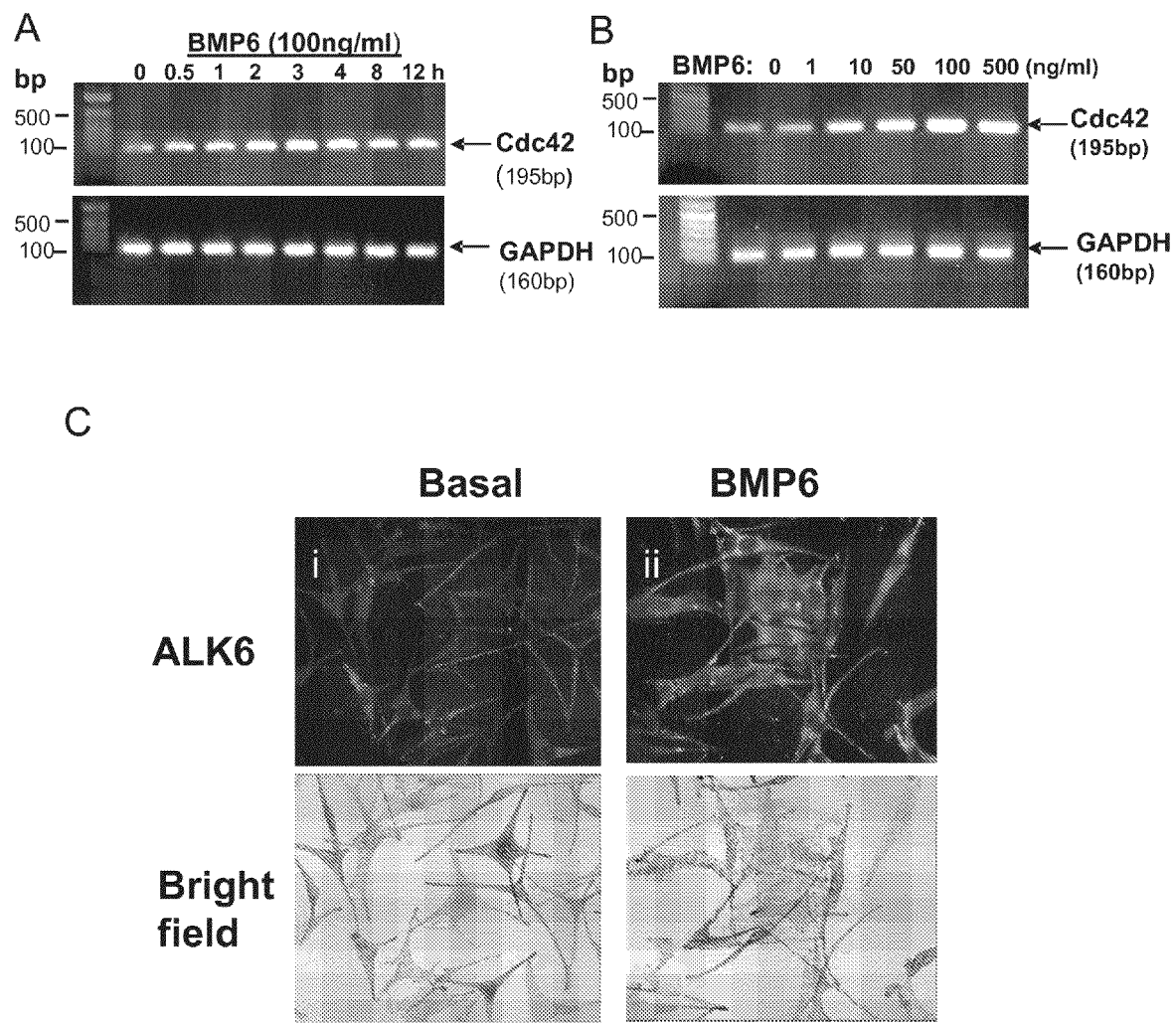

FIGS. 4 A and B show the result of and experiment to determine whether BMP6 up-regulates Cdc42 and ALK6 (the BMP6 receptor) expression in epidermal melanocytes. RT-PCR analysis of Cdc42 mRNA expression in normal human epidermal melanocyte cultures (Female 39y-MC).
- A. 100 ng/ml BMP6 treatment for the indicated times.
- B. BMP6 treatment for 2 h with the indicated dosages. Cdc42 mRNA was detected by RT-PCR. GAPDH used as an internal control for comparable loading.
- C. Normal human epidermal melanocyte cultures (Female 42y-EM) were treated for 12 h with or without 100 ng/ml of BMP6. Immunolabeling for ALK6 (green) and showing increase in the ALK6 expression under the influence of (ii) BMP6 compared to (i) untreated control. Corresponding bright-field image (lower panel).

Figure 5:
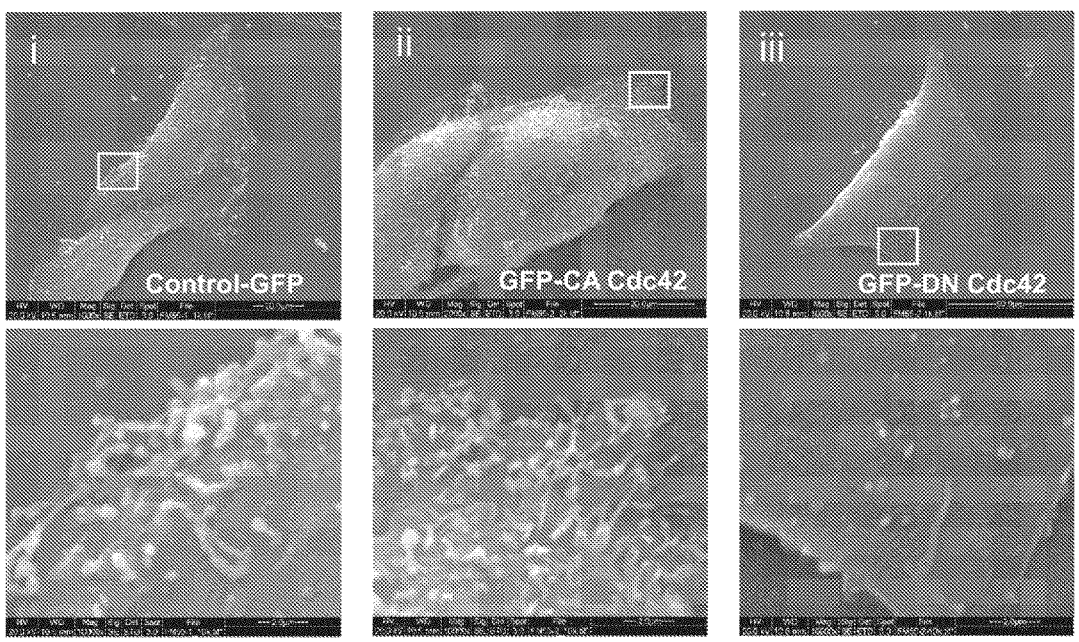
Figure 5:
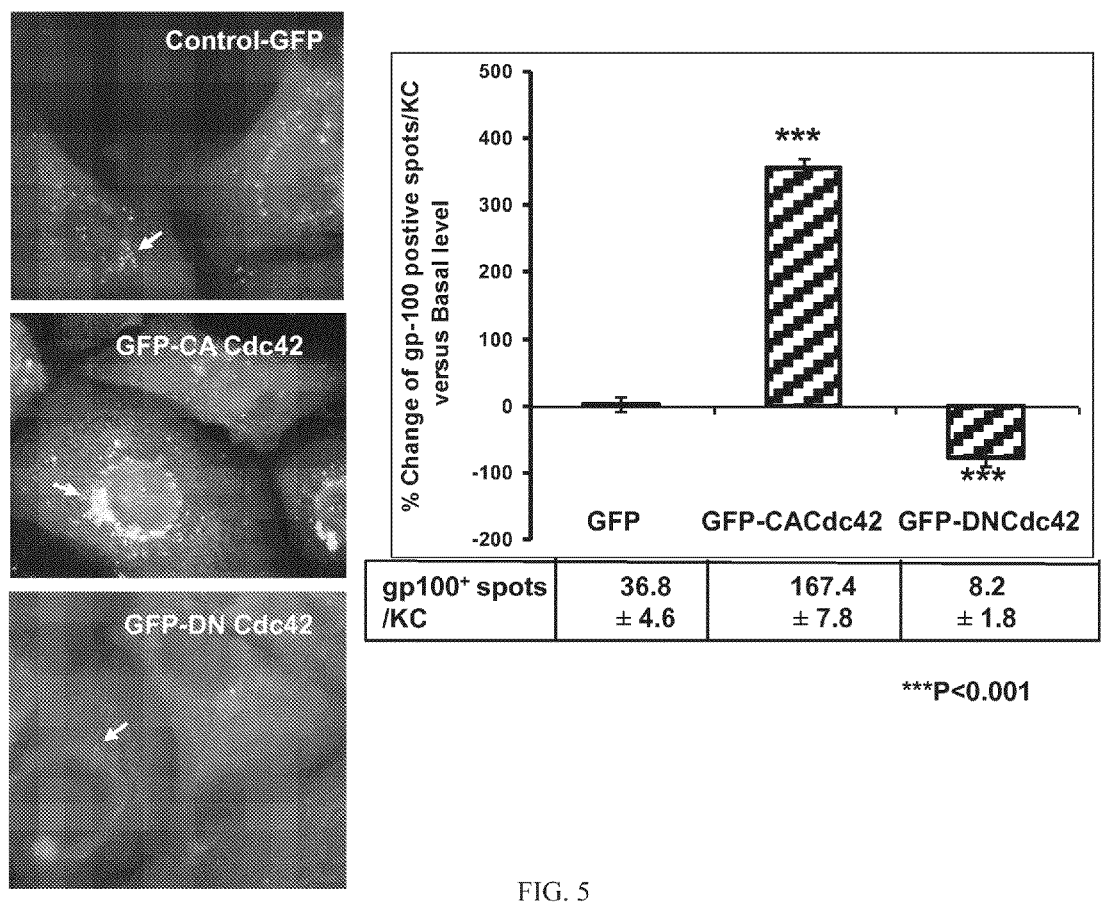

FIGS. 5 A and B, and Supplement-1 show the results of an experiment demonstrating that induction of Cdc42 expression increases dorsal filopodia formation and melanosome transfer
- A. The dorsal surface of FM55 cells transfected with (ii) Constitutively active (CA) human GFP-Cdc42(61 L) leads to a massive increase in dorsal filopodia numbers and cells transfected with (iii) Dominant negative (DN) human GFP-Cdc42 (15A) inhibited the dorsal filopodia compared to filopodia in the presence (i) GFP alone. Higher power view of boxed region (lower panel). SEM images generated using field emission SEM (FEI, Quanta 400) at accelerating voltage of 10 keV.
- B. (left panel) Double-immunofluorescence was performed on transfected FM55 cells-keratinocyte co-cultures. (i) GFP alone in FM55 and keratinocyte (ii) Constitutively active (CA) human GFP-Cdc42(61 L) in FM55 and keratinocyte and (iii) Dominant negative (DN) human GFP-Cdc42 (15A) in FM55 and keratinocyte co-cultures. Double-immunolabelling with anti-gp100 antibody (green) and anti-cytokeratin antibody (red) revealed a clear increase in the number of fluorescent spots transferred to the keratinocytes in presence of different constructs. Nuclei were stained with DAPI.
- B. (Right panel) Quantification of transferred melanosomes in five randomly-selected microscopic fields (total 20 cells per field) for each of the different treatment groups. Values were expressed as percentage increase in the number of gp100-positive spots per keratinocyte compared to unstimulated control levels. Means are ±SEM of three independent experiments with, ***P<0.001.

Supplement 1: Selection of transfected FM55 cells were confirmed by GFP expression (green). In order to confirm the melanocytic identity transfected cells were immunolabelled with melanocyte-specific anti-HMB-45/gp100 (red). Nuclei were stained with DAPI.

Figure 6:
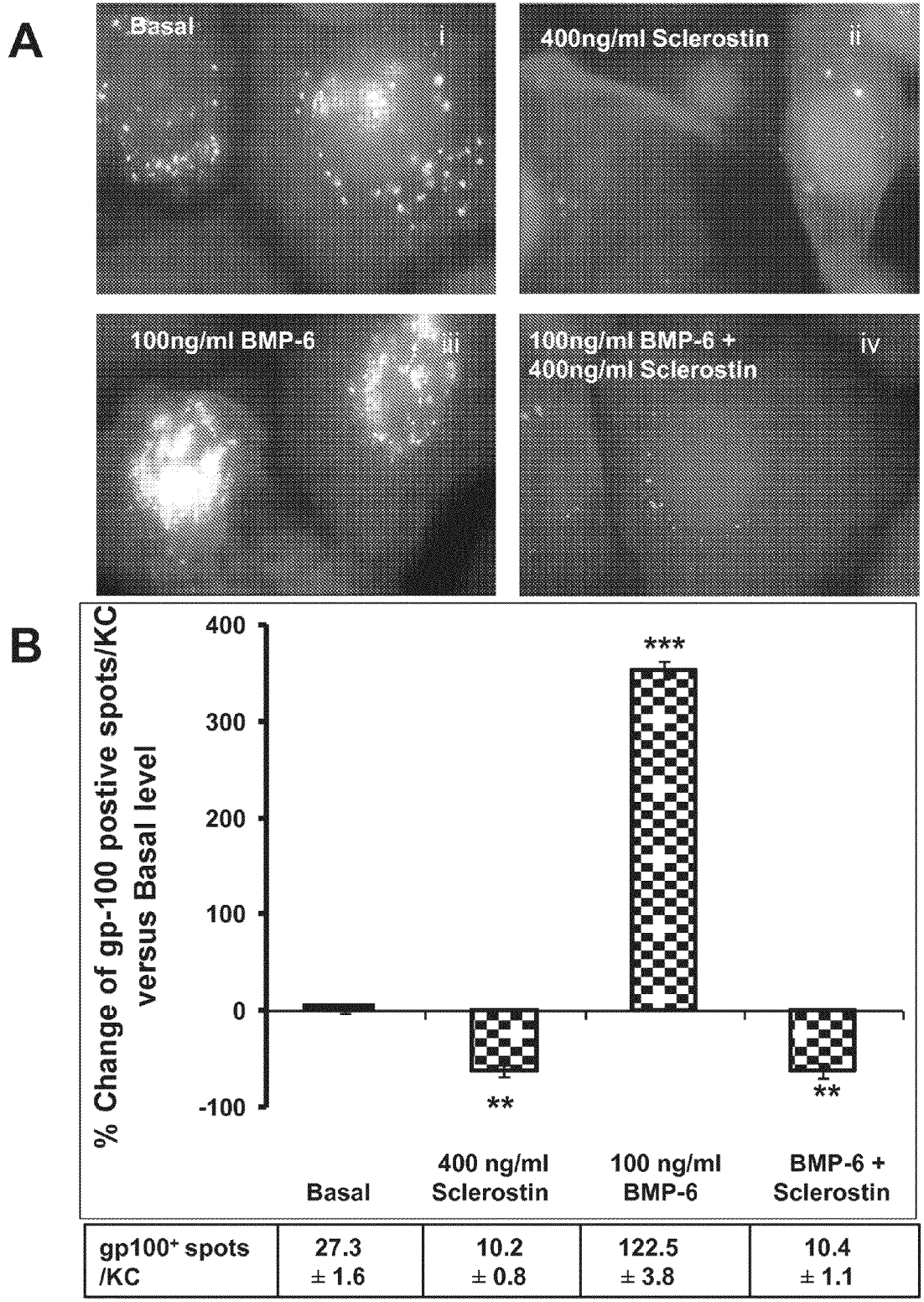

FIGS. 6 A and B show the results of an experiment demonstrating inhibition of BMP6-induced melanosome transfer using a selective BMP6 antagonist (Sclerostin)
- A. Double-immunofluorescence was performed on matched melanocyte-keratinocyte co-cultures (Female 36y MC-KC) in the presence or absence of recombinant human BMP6 (100 ng/ml) with or without addition of its selective antagonist, recombinant human Sclerostin (400 ng/ml) for 24 h. Double-immunolabelling with anti-gp100 antibody (green) and anti-cytokeratin antibody (red) revealed a clear increase in the number of fluorescent spots transferred to the keratinocytes in presence of BMP6 compared with baseline levels, which was markedly decreased when the selective antagonist Sclerostin was added to the co-culture. Nuclei were stained with DAPI.
- B. Quantification of transferred melanosomes in five randomly-selected microscopic fields (total 20 cells per field) for each of the different treatment groups. Values were expressed as percentage increase in the number of gp100-positive spots per keratinocyte compared to unstimulated control levels. Means are ±SEM of three independent experiments with P<0.01, *P<0.001.

Figure 7:
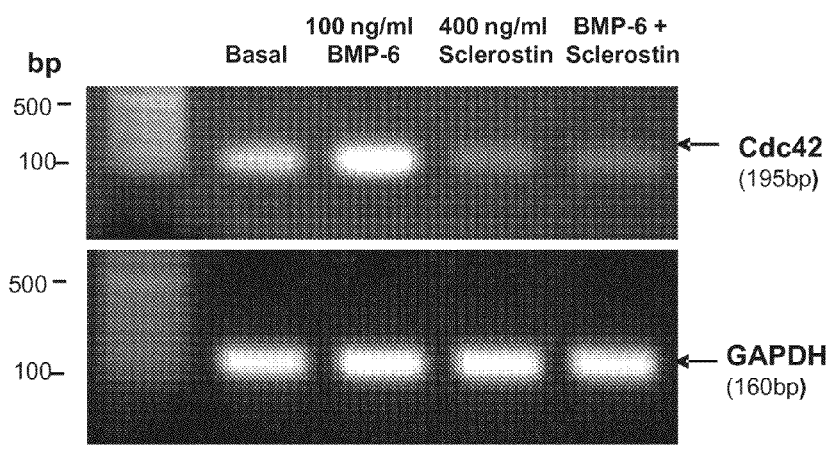
Figure 7:
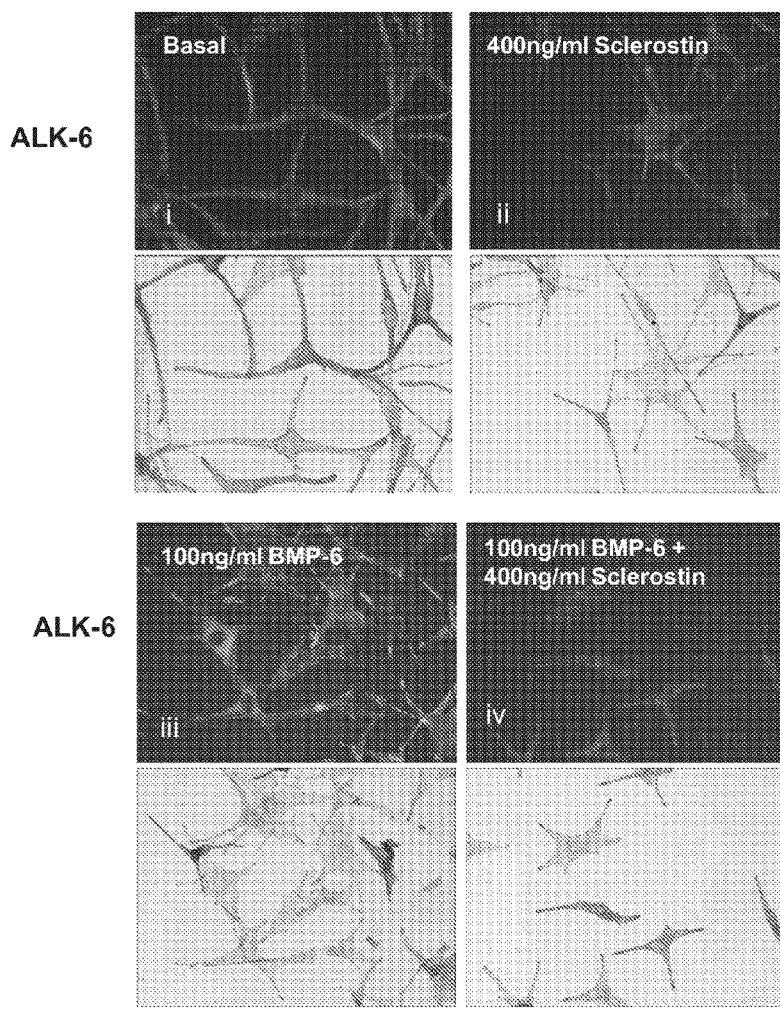

FIGS. 7 A and B show the results of an experiment demonstrating inhibition of BMP6-induced Cdc42 and ALK6 receptor expression using a selective BMP6 antagonist (sclerostin)
- A. RT-PCR analysis of Cdc42 mRNA expression:
  Normal human epidermal melanocytes (Female 42y-EM) cultured in the presence or absence of recombinant human BMP6 (100 ng/ml) with or without addition of its selective antagonist, recombinant human Sclerostin (400 ng/ml) for 2 h. Cdc42 mRNA was detected by RT-PCR and GAPDH used as an internal control for comparable loading.
- B. Normal human epidermal melanocyte cultures (Female 42y-EM) in the presence or absence of recombinant human BMP6 (100 ng/ml) with or without addition of its selective antagonist, recombinant human Sclerostin (400 ng/ml) for 12 h. Immunolabeling for ALK6 (green) and showing inhibition of BMP6-induced ALK6 expression under the influence of sclerostin. Corresponding bright-field image (lower panel).

Figure 8:
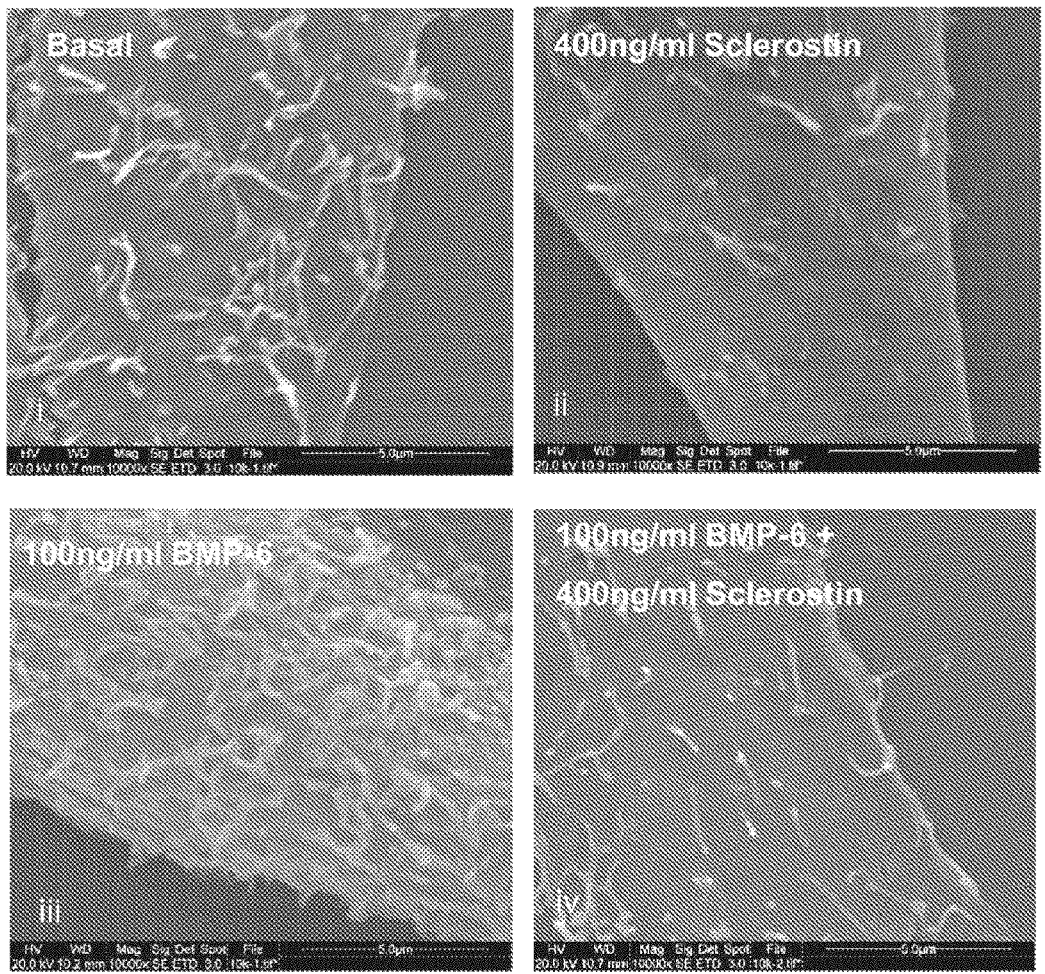

FIG. 8 shows the results of an experiment demonstrating inhibition of BMP6-induced filopodia formation using a selective BMP6 antagonist (sclerostin). Normal human epidermal melanocyte (Female 42y-EM) cultured in the presence or absence of recombinant human BMP6 (100 ng/ml) with or without addition of its selective antagonist, recombinant human Sclerostin (400 ng/ml) for 72 h. SEM images generated using field emission SEM (FEI, Quanta 400) at accelerating voltage of 10 keV.

Figure 9:
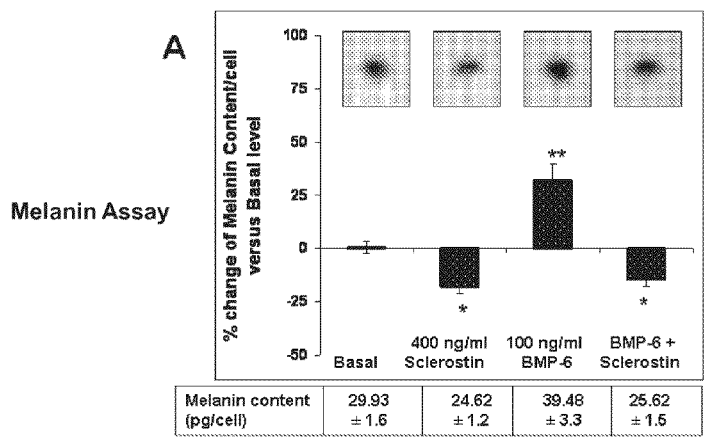
Figure 9:
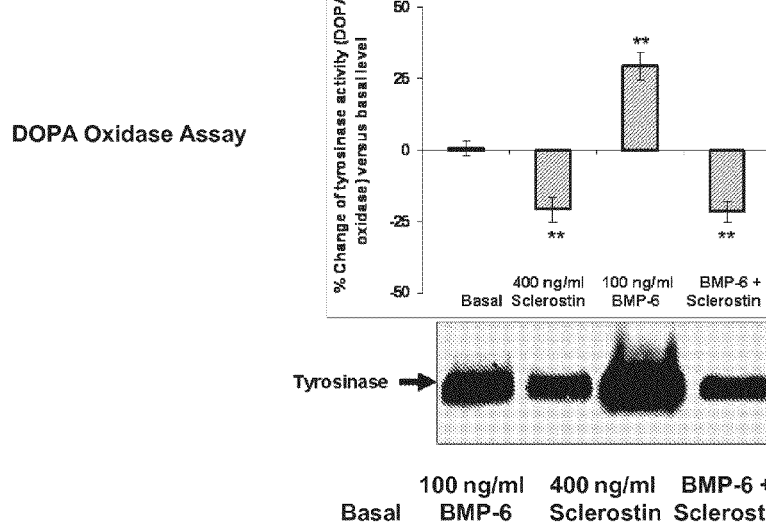
Figure 9:
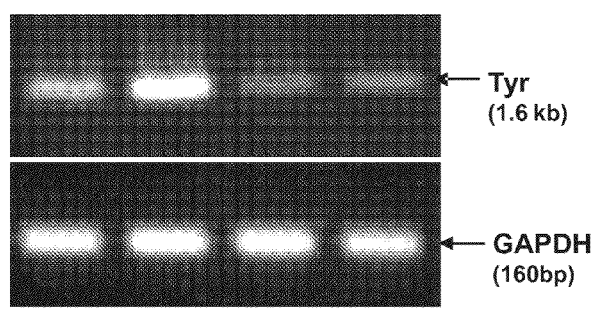
Figure 9:
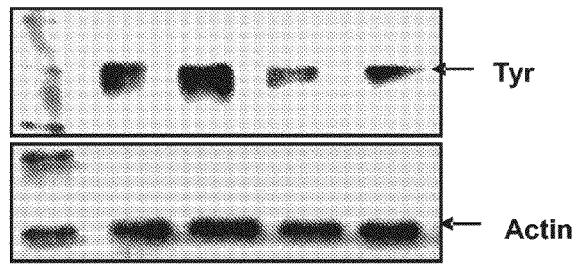

FIGS. 9 A, B and C show the results of an experiment demonstrating the effect of BMP6 on human epidermal melanogenesis, tyrosinase activity and expression of tyrosinase at mRNA and protein levels.
- A. Normal human epidermal melanocytes (F62; p4) were treated in the presence or absence of recombinant human BMP6 (100 ng/ml) with or without addition of its selective antagonist, recombinant human Sclerostin (400 ng/ml) for 72 h. Cells showed visible changes in melanin levels after treatment with different drugs. Melanin content was determined spectrophotometrically (475 nm) after sodium hydroxide solubilisation. Results were expressed as the change in melanin content (pg/cell) compared to unstimulated control levels. Means are ±SEM of 3 independent experiments with *P<0.05, **P<0.01.

B. Normal human epidermal melanocytes (Female 62y; p4) were treated in the presence or absence of recombinant human BMP6 (100 ng/ml) with or without addition of its selective antagonist, recombinant human Sclerostin (400 ng/ml) for 72 h.

(Lower panel) Protein extracts were electroblotted and membranes stained with L-DOPA for the estimation of tyrosinase activity.

(Upper panel) Densitometric scanning of band intensities and values were expressed as a fold increase compared to unstimulated control levels. Means are ±SEM of 3 independent experiments with **P<0.01.

C. Normal human epidermal melanocytes (Female 62y; p4) were treated in the presence or absence of recombinant human BMP6 (100 ng/ml) with or without addition of its selective antagonist, recombinant human Sclerostin (400 ng/ml) for 72 h.

Upper panel: Tyrosinase mRNA was detected by RT-PCR and GAPDH used as an internal control for comparable loading.

Lower panel: Tyrosinase protein was detected by Western blotting and actin used as an internal control for comparable loading.

Figure 10:
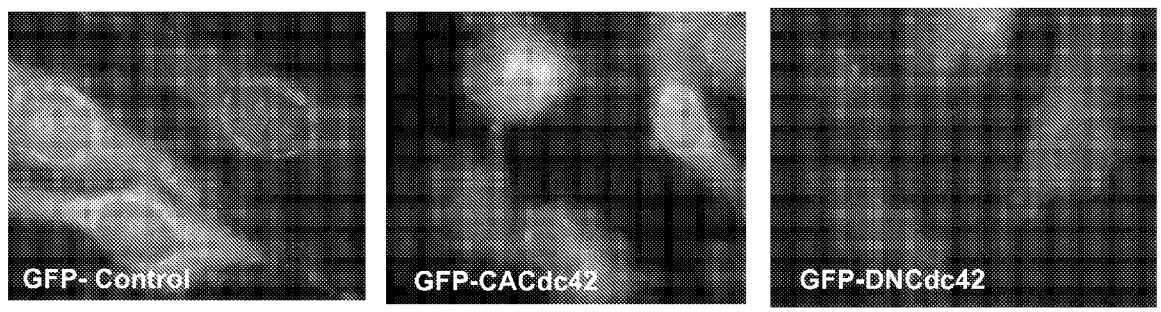

FIG. 10 shows the results of an experiment demonstrating that induction of Cdc42 expression increases dorsal filopodia formation and melanosome transfer A.

Introduction

During studies on the biology of melanin transfer the present inventors investigated the potential role of a member of the bone morphogenetic protein (BMP) family in this process. In this application a novel mechanism that controls melanin transfer from human cutaneous melanocytes to human cutaneous keratinocytes is described. This involves the action of BMP6, which can stimulate this process in a dose-dependent fashion. Moreover, the addition of a selective BMP6 antagonist (sclerostin) inhibited BMP6-induced melanosome transfer, and blocks BMP6-induced production of nanotubules (called filopodia) as evidenced by Scanning electron microscopic (SEM) analysis of human melanocytes. Dissecting the molecular mechanism by which BMP6 induces filopodia formation, it was found that BMP6 stimulates the expression of (cell division cycle 42) Cdc42 in a dose-dependent manner in human melanocytes using reverse transcriptase analysis. Requirements of Cdc42 in filopodia formation and melanosome transfer in melanocytes were verified using SEM analysis of FM55 cells with transfected constitutively active (CA) Cdc42 and dominant-negative Cdc42. CA-Cdc42 induces dorsal filopodia formation while DN-Cdc42 suppresses dorsal filopodia.

BMP6 is predicted to be synthesised as a precursor molecule which is cleaved to yield a 132 amino acid mature polypeptide with a calculated molecular weight of approximately 15 Kd. BMP6 (precursor) is a 57 kD protein, 513 amino acids in length, localized to chromosome 6p24 in human. The mature form of BMP6 contains three potential N-linked glycosylation sites per polypeptide chain. The active BMP-6 protein molecule is likely a dimer. Processing of BMP6 into the mature form involves dimerization and removal of the N-terminal region in a manner analogous to the processing of the related protein TGFβ (Gentry et al., Mol. Cell. Biol. 8: 4162 (1988). The human BMP6 precursor is provided in the GenBank database (accession number-P22004) and integrated into UniprotKB/Swiss-Prot (see SEQ ID NO: 1). The mature polypeptide is believed to include amino acids 374-513 of SEQ ID NO: 1. Other active BMP-6 polypeptides include polypeptides including amino acids 382-513,388-513 and 412-513 of SEQ ID NO: 1.

BMPs work by binding to a receptor complex that is found on the surface of almost all normal cells, and is composed of type I and type II receptors. BMPR-I, when present as a monomer, binds BMP with low affinity. However, when BMPR-I and BMPR-II are present as a heterodimer, their affinity for BMP is substantially increased (Hogan 1996). Once secreted, BMP dimers initiate signaling by binding cooperatively to both type I and type II receptors. Each monomer of BMP6 can connect to both type I and type II receptors. Thus the assembly of the tetrameric receptor complex is essential for transducinq the signal into the cell.

Type II receptors are constitutively-active kinases, which transphosphorylate type I receptors upon ligand binding. However, type I receptors activate intracellular substrates by phosphorylation, and thus determine the specificity of intracellular signals. BMPs including BMP6 can bind to 2 type I receptors include BMPR-IA (ALK-3; Seq ID 4), and BMPR-IB (ALK6; Seq ID 2). While BMPR-IA and BMP-IB are structurally similar they show distinct spatial and temporal expression patterns.

It has also been found that BMP6 induced the expression of its own cognate receptor, ALK6 (accession number 000238). A selective BMP6 antagonist sclerostin inhibited this BMP6-induced ALK6 expression along with Cdc42 expression in melanocytes, suggesting that Cdc42 participates in a possible amplification loop for BMP6 signalling. Together these findings suggest that the Cdc42 signal emanating from melanocyte BMP receptors is involved in filopodia formation to control melanosome transfer to keratinocytes.

The amino acid sequence of Sclerostin (SOST) is provided in the GenBank database (accession number-Q9BQB4) and integrated into UniprotKB/Swiss-Prot. (see SEQ ID NO: 3). The C-terminal region of SOST (amino acids 169-203 of SEQ ID 3) play a role in SOST dimerisation. The N-terminal region of SOST (amino acids 23-58 of SEQ ID 3) interacts with both type-I and type-II receptor biding sites on BMP6, and a portion of the core region (amino acids 134-166 of SEQ ID 3) may interact with the type II receptor biding site such that antibodies specific for these SOST regions may block or impair binding of BMP to SOST.

Finally, it has also been shown that BMP6 can induce melanogenesis by stimulating the expression and activity of the rate-limiting enzyme (tyrosinase) in melanocytes.

In this application it has been shown for the first time that BMP6 can control melanin transfer between melanocytes and keratinocytes, and potentially from keratinocytes to keratinocytes. This occurs, at least in part, through the action of Cdc42. BMP antagonists, and molecules based on their structure and action can be used as novel regulators of mammalian skin and hair pigmentation.

Materials & Methods

Cell Culture Isolation and Culture of Matched Epidermal Keratinocytes and Epidermal Melanocytes Human abdomen skin was obtained with informed consent and local research ethics committee approval from normal healthy Caucasian donors with skin photo-type II (female 68y, 39y, 36y) and skin photo-type VI (female 42y) after elective plastic surgery.

All cell culture reagents were obtained from Invitrogen Ltd. (Paisley, Scotland) unless otherwise stated. Skin samples were collected in RPMI 1640 medium and were processed within 5 h of surgery. Epidermal melanocytes cultures were established as previously described (Kauser et al., 2003) and grown in a mixture of K-SFM and Eagle's minimal essential medium (EMEM) supplemented with 1% FBS, 1× concentrated non-essential amino acid mixture, penicillin (100 U/ml)/streptomycin (100 µg/ml), 2 mM L-glutamine, 5 ng/ml basic fibroblast growth factor (bFGF), and 5 ng/ml endothelin-1 (Sigma, Poole, Dorset, UK). Fully matched epidermal keratinocytes (i.e. from the same skin specimen) were established as described previously (Kauser et al., 2003) and grown in keratinocyte serum-free medium (K-SFM) supplemented with 25 µg/ml bovine pituitary extract (BPE), 0.2 ng/ml rEGF, penicillin (100 U/ml)/streptomycin (100 µg/ml), and 2 mM L-glutamine. Culture medium was replenished every second day. Primary cultures of keratinocytes and melanocytes were identified using anti-cytokeratin antibody (Abcam, Cambridge, UK) and the melanocyte-specific NKI/beteb antibody (Monosan, Uden, Netherlands) to gp100 respectively.

For co-culture studies melanocytes (passage 4) and keratinocytes (passage 2) were seeded onto 8-well Lab-Tek® chamber slides (ICN Biomedicals, Inc. Aurora, Ohio, USA) at a cell density of $1\times10^4$ cells/well and in a ratio of 1 melanocyte to 10 keratinocytes. Co-cultures were maintained overnight (16 h) in a mixture of K-SFM and MEM (co-culture medium) to allow cell attachment, followed by medium replenishment for a further 24 h.

The co-cultures were incubated for 16 h in serum-starved medium (i.e., lacking foetal calf serum and bovine pituitary extract) to remove exogenous sources of growth factors, before assessing the effects of 100 ng/ml recombinant human BMP-6 (R & D System, Oxfordshire, UK) and 400 ng/ml recombinant human sclerostin (R & D System, Oxfordshire, UK) for 24 h.

Assessment of BMP-6 Doses:

Epidermal melanocytes (MC) and epidermal keratinocytes (KC) were seeded into 6-well plates in serum-supplemented full MEM melanocyte and K-SFM keratinocyte medium for 24 h. The cells were switched to serum free medium (so-called starved) supplemented with 10 ng/ml and 100 ng/ml BMP-6 for 24 h, 48 h and 72 h. Cytotoxicity was assessed by cell death and cytopathologic change in morphology.

Approximately $1\times10^4$ MC were seeded into each well of a Lab-tek® 8-well chamber slide and allowed to attach for 24 h. Cells were then washed 3-times with sterile PBS and supplemented with 350 µl of starved serum-free melanocyte medium and incubated at 37° C. and 5% $CO_2$ for 24 h. Cells were then washed with sterile PBS three times and incubated with or without 100 ng/ml of BMP-6 for 12 h. Cells were then gently washed 3-times with sterile PBS and fixed in ice-cold methanol for 10 minutes at –20° C. Slides were stored at –20° C. until immunocytochemistry was performed.

Western Blot Analysis:

MC in a confluent T225 flask were trypsinised and seeded into T25 flask with full medium and allowed to attach overnight. 24 h before treatment the medium was replaced with starved medium for 24 h. Cells were washed 3-times with sterile PBS, and incubated in starved medium alone or with 100 ng/ml of BMP-6 for different time periods (1-24 h). In a different experiment cells were treated for 12 h with different concentration of BMP-6.

40 mg of total protein from each cell extract was electrophoresed in reducing SDS-8%-PAGE and blotted on PVDF membranes (Millipore Corporation, Bedford, Mass.). The membranes were blocked with 5% milk PBS/0.075% Tween 20 for 2 h at room temperature and were then probed with primary antibodies for overnight at 4° C. The molecular weight ladder (Magik Marker, Invitrogen) was incubated in 5% milk PBS/0.075% Tween-20 and the membrane strips were incubated with either 1 ml of 5% milk PBS/0.075% Tween-20 (negative control), or 1 ml of rabbit anti-tyrosinase (1:200 polyclonal antibody in 5% milk PBS/0.075% Tween 20) and 1 ml of goat anti-actin (1:1000 polyclonal antibody in 5% milk PBS/0.075% Tween 20) on a rocking platform overnight at 4° C. After extensive washes the blots were incubated with horseradish peroxidise conjugated secondary antibodies for 2 h. The molecular weight ladder was then incubated with 1 ml of HRP-goat anti-human IgG (H+L) (Zymed, USA) (1:500) diluted in 5% milk PBS/0.075% Tween 20 and membrane strips were incubated in 1 ml of anti-rabbit IgG, horseradish peroxidase linked whole antibody (HRP) secondary antibody (Amersham Biosciences, UK) (1:700 diluted in 5% milk PBS/0.075% Tween 20) on a rocking platform for 2 hours at room temperature. The washing procedure was repeated and the membrane strips were incubated in Lumi-GLO® Reagent and Peroxide (BioLab Ltd, UK) for 2 minutes at room temperature. The chemiluminescent signal was detected by exposing the blot strips to Kodak XRA X-ray film (Kodak, UK) at various exposure times, followed by development in developing solution (Kodak, UK) until bands appeared, rinsed in tap water, fixed in the fixer (Kodak, UK) until the film turned blue, then rinsed with tap water and allowed to dry. The membrane was then labelled and scanned for densitometric analysis for the semi-quantitative assessment of protein expression levels using analysis software (Image Master Total lab version 1.11).

Immunofluorescence Staining:

Cells fixed in ice-cold methanol were washed in PBS and then blocked with 10% donkey serum for the detection of protein expression. For double labelling experiments the first primary antibody, either BMP-6 (Abcam, Cambridge, UK), BMPR-IB/ALK-6 (R & D Systems, Oxfordshire, UK) or NKi/beteb (1:30) (Monosan, Uden, Netherlands) was applied overnight at 4° C., followed by incubation with FITC-conjugated secondary antibody (1:100) for 1 h at room temperature. The second primary antibody, either cytokeratin (1:100) (Abcam, Cambridge, UK) or β-Actin (1:100) (Santa Cruz, USA) was applied for 1 h at room temperature followed by a TRITC-conjugated secondary antibody (1:100) (Jackson Immunoresearch Laboratories, Inc., West Grove, USA). DAPI (Vector Laboratories, Burlingame, Calif.) was used to stain nuclei. Images were captured with a cooled Hamamatsu digital camera using a 100× or 40× objectives and post-processed using Paint Shop Pro (Jasc Software Ver. 7. CA, USA). Negative controls included the omission of primary antibody and replacement with non-immune serum from secondary antibody host and inclusion of secondary antibodies.

Quantitative Analysis of Melanosome Transfer:

Matched melanocytes-keratinocytes co-cultures were stimulated with different doses of BMP-6 and compared with unstimulated cells. Evaluation of melanosome transfer was performed by counting fluorescent gp100-positive spots within recipient keratinocytes in 5 random microscopic fields per well at 100× magnification (oil-immersion) in 3 independent experiments. To avoid counting melanin granules that may still be associated with melanocytes, we only counted gp100-positive spots within keratinocytes that were not in direct contact with melanocytes.

Reverse Transcription-Polymerase Chain Reaction (RT-PCR)

Total RNA was obtained from $1\times10^6$ melanocytes treated with either 1-, 10-, 50-, 100- and 500 ng/ml BMP6 for 4 h or 100 ng/ml BMP6 for indicated time period (FIG. 4A). For some experiments melanocytes were also treated with or without 400 ng/ml of Sclerostin either in the presence or absence of 100 ng/ml BMP6. RNA samples were treated with deoxyribonuclease (QIAGEN, UK), followed by determination of concentration. Then a Superscript III First-Strand synthesis for Reverse Transcription Kit (Invitrogen, California) was used to synthesize first strand cDNA. The final concentration of RNA in the reaction was 1 μg/100 μl for all samples. PCR was performed with QIAGEN Fast Cycling PCR kit (QIAGEN, UK) under conditions described by manufacturer. Briefly, the following cycling conditions were used: 95° C. for 15 min (stage1); 96° C. for 15 s; primer annealing for 15 s (For Cdc 42-65° C., Tyrosinase-58° C. and GAPDH-60° C.); 72° C. for 25 s (stage 2)×30 cycle. Primers used for RT-PCR reactions are shown in Table 1 and were obtained from Sigma-Genosys, UK. PCR products were separated over 1% agarose gel in 1×TAE buffer and stained with ethidium bromide. 1 Kb DNA Plus DNA ladder (Invitrogen, California) were used as a DNA marker.

TABLE 1

Primer for semi-quantitative RT-PCR

| Gene | Forward Primer | Reverse Primer | Product Length (bp) |
|---|---|---|---|
| 1. Cdc42 | GCCCGTGACCTGAAGGCT-GTCA (SEQ ID NO: 5) | TGCTTTTAGTATGATGCCGACACCA (SEQ ID NO: 6) | 195 |
| 2. Tyrosinase | CACCCCACAAATCCTAAC (SEQ ID NO: 7) | CCTACTCTATTGCCTAAGCC (SEQ ID NO: 8) | 180 |
| 3. GAPDH | GAAGGTGAAGGTCGGAGTACA (SEQ ID NO: 9) | TTGTTTTGGAGGGATCTCG (SEQ ID NO: 10) | 160 |

Transfection

Dominant-negative human GFP-Cdc42(15A) and the constitutively active GFP-Cdc42(61 L) and GFP in pEGFP-C3 were generous gifts of Richard E. Cheney (University of North Carolina, Chapel Hill). Vectors included the neomycin gene conferring resistance to geneticin (G418). Approximately $5 \times 10^5$ moderately pigmented FM55 cells were grown to 70-80% confluence in six well plates for 16 h in RPMI medium with 10% FBS day before transfection. FM55 cells were transfected using Lipfectamine 2000 Transfection Reagent (Invitrogen, Carlabad, Calif., USA). Briefly, 3.2 μg of cDNA constructs was mixed with 8 μl of Lipfectamine 2000 Transfection Reagent in 1.6 ml of Opti-MEM Reduced Serum Medium. Cells were incubated with transfection mixture for 12 h, washed three times with 1×PBS, incubated in fresh RPMI containing 10% FBS for 48 h. The transfected cells were selected for 15 days using 1.6 mg/ml G418. Then $1 \times 10^4$ stable transfected cells were cultured for 24 h in 8-well Lab-Tek® chamber slides in the presence of RPMI medium with 10% FBS. After 24 hrs stably-transfected cells were immediately fixed in 1% glutaraldehyde (Sigma, UK) buffered in 0.1 M sodium cacodylate (Agar, UK) at 37° C. in order to conserve shape conformation (including filopodia) of FM55 cells and processed for SEM analysis. Parallel cells on 8-well Lab-Tek® chamber slides were also fixed in ice-cold methanol for 10 min at −20° C., washed in PBS and then blocked with 10% donkey serum for gp100 immunofluorescence studies to verify transfection and selection. For co-culture studies stably-transfected FM55 cells and keratinocytes (passage 2) were seeded onto 8-well Lab-Tek® chamber slides at a cell density of $1 \times 10^4$ cells/well and in a ratio of 1 FM55 to 10 keratinocytes. Co-cultures were maintained overnight (16 h) in a mixture of K-SFM and MEM (co-culture medium) to allow cell attachment, followed by medium replenishment for a further 24 h. Cells were then fixed in ice-cold methanol for 10 min at −20° C., washed in PBS and then blocked with 10% donkey serum for gp100 and cytokeratin double immunofluorescence studies to test melanosome transfer efficiency.

Scanning Electron Microscopic Assessment of Cell Morphology

Epidermal melanocytes treated with or without 400 ng/ml of Sclerostin either in the presence or absence of 100 ng/ml BMP6 for 72 h and stably-selected transfected FM55 cells were fixed with 1% glutaraldehyde (Sigma, UK) buffered in 0.1 M sodium cacodylate (Agar, UK) at 37° C. The cells were then post-fixed in 1% osmium tetroxide (Agar, UK) and 1% tannic acid (Agar, UK) used as mordant, dehydrated through a series of alcohol from 20 to 70%, stained in 0.5% uranyl acetate, followed by further dehydration in 90 and 100% alcohol. The final dehydration was in hexamethyl-disilazane (Sigma, UK), followed by air drying. Once dry, samples were coated with gold in a gold sputter (EMITECH, K550) (Blazer 20 mA) for 10 minutes. Specimens were viewed under field emission SEM (FEI, Quanta 400) at accelerating voltage of 10 keV.

Melanin Assay

500 μg/ml of synthetic melanin (Sigma, UK) was prepared in 1 M sodium hydroxide (NaOH) (BOH Ltd, UK) and dissolved in a sonicating water bath for 20 minutes. From this stock solution, various melanin standards were prepared in 1 M NaOH from 100 μg/ml to 1 μg/ml. The melanin standards were pipetted into a 96 well plate to produce a calibration curve for the assessment of melanin content in the test samples. 400 μl of 1 M NaOH was added to each cell pellet and dissolved on a heat block (100° C.) for 15 minutes. The pellets were vortexed vigorously and the solibulized pellet was pipetted into the same 96-well plate. The optical densities of the sample were read at 495 nm on a DYNEX REVELATION 4.02 program. Melanin content of each test sample was read from the calibration curve.

DOPA Oxidase Detection Using Non-Denaturing SDS-PAGE for Assessment of Tyrosinase Activity Approximately $1 \times 10^6$ of epidermal melanocytes, were seeded into three T75 flasks and were incubated at 37° C. and 5% $CO_2$ overnight. The cells were prepared for SDS-PAGE and transblotted onto PVDF membranes. 70 μg of un-reduced protein extract without boiling was pipetted into the appropriate wells of 8% SDS-PAGE gels. The PVDF membrane containing the separated proteins was washed once in 1×PBS and then incubated at RT in 5 mM L-DOPA in 0.1 M sodium phosphate buffer for 3 hours with three changes of the L-DOPA. The L-DOPA reaction was stopped by washing the membrane in distilled water and the membrane was scanned.

Statistical Analysis:

Statistical significance between groups and treatment was assessed using one-way ANOVA and Dunnett's post-test using Prism v. 4.00 (Graph Pad Software Chicago, Ill., USA). Statistically significant differences are denoted with asterisks: =P<0.01, *=P<0.001.

Results and Discussion

BMP6 (10 and 100 ng/ml) does not Exhibit Cytotoxicity to Normal Human Epidermal Melanocytes and Keratinocytes To rule out the possibility that BMP6 is toxic to melanocytes or keratinocytes, cells were maintained in the presence of 10 ng/ml and 100 ng/ml for 24 h, 48 h and 72 h. Both doses of BMP6 are not associated with altered cell growth or morphology of melanocyte and keratinocytes (FIG. 1A, 1B).

Normal Human Epidermal Melanocytes Express BMP6 Protein and Receptor ALK6

Expression of BMP6 in normal human melanocytes was confirmed by double immunolabeling (yellow-orange, Aiii) of anti-BMP6 (green, Ai) with anti-tyrosinase antibody (red, Aii) (FIG. 2A). Double immunolabeling of melanocytes with anti-BMP6 (green, Bi) and anti-ALK6 (Red, Bii) antibody revealed BMP6 and ALK6 co-localization (yellow, Biii) throughout the cell (FIG. 2B).

Quantitative Analysis of Dose-Dependent BMP6-Stimulated Melanosome Transfer

The ALK6 receptors are functional, as BMP6 treatment on melanocyte-keratinocyte co-culture leads to stimulation of melanosome transfer from melanocytes to keratinocytes in a dose-dependent fashion (FIG. 3 A, B). Thus this is the first report of an effect of BMP6 on melanosome transfer in melanocyte-keratinocyte co-culture system. Both autocrine and paracrine effects may be involved.

BMP6 Up-Regulates Cdc42 Message Expression in Human Epidermal Melanocytes

To better understand the mechanistic roles of BMP6 in melanosome transfer, we investigated the expression of Cdc42; a master regulator of filopodia formation in human melanocytes (Scott et al., 2002). RT-PCR analysis indicated that maximum induction of Cdc42 after 100 ng/ml BMP6 treatment occurred from 2-4 h and then reduced slightly but remain elevated for up to 12 h, compared with the basal level expression of Cdc42 mRNA in untreated control (FIG. 4 A). The induction of Cdc42 mRNA by BMP6 occurred in a dose-dependent fashion (FIG. 4B). BMP6-also stimulated the expression of the BMP6 receptor ALK6 (green FIG. 4C ii) compared to normal basal level of expression of ALK6 (Figure C i) in normal human epidermal melanocytes (FIG. 4C).

Requirement of Cdc42 to Stimulate Melanosome Transfer by Inducing Dorsal Filopodia Two kinds of Rho protein mutants have been used extensively to analyze their functions; activated mutants, which are constitutively GTP-bound because the GTPase activating proteins (GAPs) are inhibited; and dominant-negative mutants which act by titrating out guanine nucleotide exchange factor (GEFs) (Feig 1999). We have found that constitutively active Cdc42 induces dorsal filopodia and that dominant-negative Cdc42 suppresses dorsal filopodia of FM55 human melanoma when compared with the control vector (FIG. 5 A).

We were next keen to determine whether over-expression of Cdc42 proteins can also affect the melanosome transfer. In order to test the involvement of these over-expressed proteins in melanin transfer, transfected FM55 cells were used to establish the FM55 melanoma-keratinocytes co-cultures for 24 h. Immunolabelling of this co-culture with anti-gp100 antibody (green) showed clear changes in the number of fluorescent spots transferred to keratinocytes (white arrow) (FIG. 5B, left panel). Constitutively active GFP-Cdc42 induces the melanosome transfer while dominant-negative GFP-Cdc42 inhibited the melanosome transfer compared with GFP control vector (FIG. 5B, right panel). Manipulation of melanosomes transfer by over-expression or inhibition of Cdc42 further suggests the strong involvement of filopodia in melanosome transfer. Since BMP6 can up-regulate the expression of Cdc42, this suggests that BMP6-associated stimulation of melanosome transfer may involve Cdc42 as its downstream target. To test this we exploited the inhibitory effect of DN-Cdc42 on filopodia formation and melanosome transfer. This can also be similarly achieved by knocking down of endogenous Cdc42 expression of human melanocyte using a siRNA against human Cdc42.

Inhibition of BMP6-Induced Melanosome Transfer Using a Selective BMP6 Antagonist (Sclerostin)

To test whether or not sclerostin (a selective BMP6 antagonist) inhibits BMP-6-induced melanosome transfer, we tested this antagonist in normal human epidermal melanocyte-keratinocyte co-culture. The addition of sclerositin itself inhibited the basal level of melanosome transfer from melanocytes to keratinocytes (FIG. 6A,B). Moreover, sclerostin inhibited the BMP6-induced melanosome transfer in human epidermal melanocyte-keratinocyte co-culture suggesting that sclerostin can be used as a novel regulatior of mammalian skin and hair pigmentation (FIG. 6A, B).

Inhibition of BMP6-Induced Cdc42 and ALK6 Receptor Expression Using a Selective BMP6 Antagonist (Sclerostin)

We have shown first time about the physiological role of Cdc42 as a regulator of melanosome transfer from melanocytes to keratinocytes (FIG. 5B). The ability of sclerostin to inhibit BMP6-induced melanosome transfer suggested that sclerostin might block BMP6-induced expression of Cdc42 in human melanocytes. Using RT-PCR analysis of human melanocytes, we have indeed found that sclerostin down-regulated BMP6-induced expression of Cdc42 (FIG. 7A). Using immunofluorescence study we have also found that sclerostin down-regulated the BMP6-induced expression of ALK6 (green), a BMP6 receptor (FIG. 7B). This finding suggests that Cdc42 participates in a possible amplification loop for BMP6 signalling.

Inhibition of BMP6-Induced Filopodia Formation Using a Selective BMP6 Antagonist (Sclerostin)

SEM analysis of melanocytes exhibits stimulation of numerous dorsal filopodia by BMP6 treatment compared to untreated control (FIG. 8iii). Melanocytes treated with sclerostin exhibited a reduction in dorsal filopodia formation, whereas cells treated with the BMP6 did not induce filopodia formation in the presence of sclerostin (FIG. 8 ii, iv). These data strongly support the requirement of BMP6 for stimulation of dorsal filopodia formation of in human melanocytes.

Together with the inhibition of BMP6-induced melanosome transfer (FIG. 6), inhibition of Cdc42 and ALK6 receptor expression (FIG. 7) and inhibition of filopodia formation (FIG. 8) by sclerostin suggest that the Cdc42 signal emanating from melanocyte BMP receptors are involved in filopodia formation that control melanosome transfer to keratinocyte.

Effect of BMP6 on Melanogenesis in Human Epidermal Melanocytes

BMP6 increased melanin content (by approx. 32±9% after 72 h) in human epidermal melanocytes in vitro (FIG. 9A). A selective BMP6 antagonist sclerostin inhibited the BMP6-induced melanin content (by 15±3%), in human epidermal melanocytes (FIG. 9A). Tyrosinase activity (an indicator of melanin synthesis potential) was also stimulated by BMP6 while Sclerostin inhibited BMP6-induced increase in tyrosinase activity (FIG. 9B).

Summary: The study of signalling mechanisms for induction of melanogenesis in melanocyte indicated that cAMP elevating agents, acting through protein kinase A, induced melanogenesis in melanocytes by increasing the expression of tyrosinase (Bertolotto et al., 1998). Beyond this simplified scheme, p38 MAPK cascade was also demonstrated to be involved in melanogenesis in melanocytes by treatment with MSH, UV light or human placental sphingolipid (Galibert et al., 2001; Smalley and Eisen, 2000; Singh et al., 2005).

Recently BMPs are also emerging as a strong regulator of melanogenesis (Botchkarev 2003; Yaar et al., 2006). BMP4 has been found to be act as an autocrine inhibitor of melanogenesis in normal human melanocytes by inhibiting the expression and activity of the rate-limiting enzyme (tyrosinase) in melanocytes (Yaar et al., 2006). In our study we have found that BMP6 act as a stimulator of melanogenesis by stimulating the expression of tyrosinase at both protein and gene level (FIG. 9C). While sclerostin inhibited the BMP6-induced tyrosinase expression in human epidermal melanocytes at both protein and gene level (FIG. 9C).

---

The invention claimed is:

1. A method of increasing melanin pigmentation of the skin of a subject, the method comprising topically administering to the subject, a composition substantially comprising BMP6 (SEQ ID NO:1), or a fragment or variant thereof, wherein said variant has at least 70% sequence identity with BMP6 (SEQ ID NO:1) and wherein said composition exhibits the ability to increase melanogenesis or melanin transfer by modulating the activity or expression of ALK6 or Cdc42.

2. The method of claim 1, wherein the composition modulates the expression of Cdc42 through modulating the activity of ALK6.

3. The method of claim 1, wherein the method is a cosmetic method of cosmetic darkening of skin through modulating the level of melanin pigmentation of the skin.

4. The method of claim 1, wherein the composition is capable of increasing the activity of ALK6 relative to normal physiological levels.

5. The method of claim 1, wherein the method comprises administering to a subject a composition comprising a fragment of precursor BMP6 selected from the group consisting of amino acids 374-513 of SEQ ID NO: 1, amino acids 382-513 of SEQ ID NO: 1, amino acids 388-513 of SEQ ID NO: 1, and amino acids 412-513 of SEQ ID NO: 1.

6. The method of claim 1, the method comprising topically administering to a subject a composition substantially comprising amino acids 374-513 of SEQ ID NO: 1, or a fragment or variant thereof, where said variant has at least 70% sequence identity with amino acids 374-513 of SEQ ID NO: 1, and wherein said fragment or variant exhibits the ability to increase melanogenesis or melanin transfer.

7. The method of claim 1, the method comprising topically administering to a subject a composition substantially comprising amino acids 382-513 of SEQ ID NO: 1, or a fragment or variant thereof, where said variant has at least 70% sequence identity with amino acids 382-513 of SEQ ID NO: 1, and wherein said fragment or variant exhibits the ability to increase melanogenesis or melanin transfer.

8. The method of claim 5, wherein the composition modulates the expression of Cdc42 through modulating the activity of ALK6.

9. The method of claim 5, wherein the method involves application of the composition to the outer surface of the skin of a subject.

10. The method of claim 5, wherein the method is a cosmetic method of cosmetic darkening of skin through modulating the level of melanin pigmentation of the skin.

11. The method of claim 5, wherein the composition is capable of increasing the activity of ALK6 relative to normal physiological levels.

* * * * *